United States Patent
Dolan et al.

(10) Patent No.: US 9,743,924 B2
(45) Date of Patent: Aug. 29, 2017

(54) SYSTEMS AND METHODS FOR SUTURING TISSUE

(71) Applicant: SafePath Medical, Inc., Amesbury, MA (US)

(72) Inventors: David P. Dolan, Londonderry, NH (US); Dan Morgan, Salem, MA (US); Joseph P Lane, Amesbury, MA (US)

(73) Assignee: SAFEPATH MEDICAL, INC., Amesbury, MA (US)

( * ) Notice: Subject to any disclaimer, the term of this patent is extended or adjusted under 35 U.S.C. 154(b) by 51 days.

(21) Appl. No.: 14/715,081

(22) Filed: May 18, 2015

(65) Prior Publication Data
US 2015/0335326 A1    Nov. 26, 2015

Related U.S. Application Data

(60) Provisional application No. 61/994,890, filed on May 17, 2014, provisional application No. 62/149,532, filed on Apr. 18, 2015.

(51) Int. Cl.
| | | |
|---|---|---|
| *A61B 17/04* | (2006.01) | |
| *A61B 17/12* | (2006.01) | |
| *A61B 17/062* | (2006.01) | |
| *A61B 17/06* | (2006.01) | |

(52) U.S. Cl.
CPC ...... *A61B 17/0482* (2013.01); *A61B 17/0493* (2013.01); *A61B 17/0625* (2013.01); *A61B 2017/0608* (2013.01)

(58) Field of Classification Search
CPC ............ A61B 17/0482; A61B 17/0493; A61B 17/062; A61B 2017/0608; A61B 17/0469; A61B 17/0625

USPC ................................ 606/139, 144, 145, 148
See application file for complete search history.

(56) References Cited

U.S. PATENT DOCUMENTS

| | | |
|---|---|---|
| 1,676,582 A | 7/1928 | Stuart |
| 2,336,690 A | 12/1943 | Karle |
| 4,109,428 A | 8/1978 | Aarons |
| 4,373,530 A | 2/1983 | Kilejian |
| 4,406,237 A | 9/1983 | Eguchi et al. |
| 4,414,908 A | 11/1983 | Egochi et al. |
| 4,608,800 A | 9/1986 | Fredette |
| 4,621,640 A | 11/1986 | Mulhollan et al. |
| 4,957,498 A | 9/1990 | Caspari et al. |
| 4,969,302 A | 11/1990 | Coggan et al. |
| 5,234,443 A | 8/1993 | Phan et al. |
| 5,426,901 A | 6/1995 | Indracek |

(Continued)

OTHER PUBLICATIONS

U.S. Appl. No. 12/833,006, filed Jul. 9, 2011, McClurg et al.

*Primary Examiner* — Katherine M Shi
(74) *Attorney, Agent, or Firm* — Leason Ellis LLP

(57) ABSTRACT

A device for suturing tissue includes a handle including a housing and a suturing needle for advancing a suture through the tissue. The device also includes a first needle gripper that is configured to both grasp and release the suturing needle. A second needle gripper is also configured to both grasp and release the suturing needle. An actuator is coupled to the housing and is operatively coupled to: (a) a first linkage that pivots the second gripping gripper between a fully extended position and a retracted position relative to the housing; and (b) a second linkage that is operatively coupled to the first and second needle grippers and configured to alter a state of each of the first and second needle grippers. The second linkage can include a one-way clutch.

35 Claims, 25 Drawing Sheets

(56) References Cited

U.S. PATENT DOCUMENTS

| | | |
|---|---|---|
| 5,437,681 A | 8/1995 | Meade et al. |
| 5,457,923 A | 10/1995 | Logan et al. |
| 5,499,990 A | 3/1996 | Schülken et al. |
| 5,571,090 A | 11/1996 | Sherts |
| 5,571,119 A | 11/1996 | Atala |
| 5,609,597 A | 3/1997 | Lehrer |
| 5,643,292 A | 7/1997 | Hart |
| 5,665,109 A | 9/1997 | Yoon |
| 5,694,726 A | 12/1997 | Wu |
| 5,709,693 A | 1/1998 | Taylor |
| 5,728,113 A | 3/1998 | Sherts |
| 5,729,933 A | 3/1998 | Strength |
| 5,730,747 A | 3/1998 | Ek et al. |
| 5,746,751 A | 5/1998 | Sherts |
| 5,759,188 A | 6/1998 | Yoon |
| 5,766,186 A | 6/1998 | Faraz et al. |
| 5,824,009 A | 10/1998 | Fukuda et al. |
| 5,843,100 A | 12/1998 | Meade |
| 5,860,992 A | 1/1999 | Daniel et al. |
| 5,871,488 A | 2/1999 | Tovey et al. |
| 5,904,692 A | 5/1999 | Steckel et al. |
| 5,908,428 A | 6/1999 | Scirica et al. |
| 5,919,202 A | 7/1999 | Yoon |
| 5,935,149 A | 8/1999 | Ek |
| 5,951,575 A | 9/1999 | Boldue et al. |
| 5,954,733 A | 9/1999 | Yoon |
| 5,957,937 A | 9/1999 | Yoon |
| 5,984,932 A | 11/1999 | Yoon |
| 5,993,466 A | 11/1999 | Yoon |
| 5,993,467 A | 11/1999 | Yoon |
| 6,026,616 A | 2/2000 | Gibson |
| 6,048,351 A | 4/2000 | Gordon et al. |
| 6,071,289 A | 6/2000 | Stefanchik et al. |
| 6,099,550 A | 8/2000 | Yoon |
| 6,099,553 A | 8/2000 | Hart et al. |
| 6,159,224 A | 12/2000 | Yoon |
| 6,224,614 B1 | 5/2001 | Yoon |
| 6,277,132 B1 | 8/2001 | Brhel |
| 6,533,795 B1 | 3/2003 | Tran et al. |
| 6,539,675 B1 | 4/2003 | Gile |
| 6,643,990 B2 | 11/2003 | Jensen |
| 6,911,034 B2 | 6/2005 | Nobles et al. |
| 6,923,819 B2 | 8/2005 | Meade et al. |
| 6,984,237 B2 | 1/2006 | Hatch et al. |
| 6,997,932 B2 | 2/2006 | Dreyfuss et al. |
| 7,011,668 B2 | 3/2006 | Sancoff et al. |
| 7,033,370 B2 | 4/2006 | Gordon et al. |
| 7,060,077 B2 | 6/2006 | Gordon et al. |
| 7,090,686 B2 | 8/2006 | Nobles et al. |
| 7,108,700 B2 | 9/2006 | Chan et al. |
| 7,188,454 B2 | 3/2007 | Mowery et al. |
| 7,316,694 B2 | 1/2008 | Reinitz |
| 7,318,282 B2 | 1/2008 | Pulte |
| 7,326,221 B2 | 2/2008 | Sakamoto et al. |
| 7,331,970 B2 | 2/2008 | Almodovar et al. |
| 7,338,504 B2 | 3/2008 | Gibbens et al. |
| 7,442,198 B2 | 10/2008 | Gellman et al. |
| 7,544,199 B2 | 6/2009 | Bain et al. |
| 7,572,265 B2 | 8/2009 | Stone et al. |
| 7,582,096 B2 | 9/2009 | Gellman et al. |
| 7,588,583 B2 | 9/2009 | Hamilton et al. |
| 7,615,059 B2 | 11/2009 | Watschke et al. |
| 7,628,796 B2 | 12/2009 | Shelton et al. |
| 7,704,262 B2 | 4/2010 | Bellafiore et al. |
| 7,748,179 B2 | 7/2010 | Schiedegger et al. |
| 7,793,475 B2 | 9/2010 | Riggs |
| 7,997,043 B1 | 8/2011 | MacMillan et al. |
| 7,998,149 B2 | 8/2011 | Hamilton et al. |
| 8,006,441 B2 | 8/2011 | Pulte |
| 8,172,860 B2 | 5/2012 | Zung et al. |
| 8,252,007 B2 | 8/2012 | Hamilton et al. |
| 8,257,371 B2 | 9/2012 | Hamilton et al. |
| 8,317,805 B2 | 11/2012 | Hamilton et al. |
| 8,419,754 B2 | 4/2013 | Laby et al. |
| 8,603,113 B2 | 12/2013 | Hamilton et al. |
| 8,617,187 B2 | 12/2013 | Hamilton et al. |
| 8,685,045 B2 | 4/2014 | Hamilton et al. |
| 2002/0087178 A1 | 7/2002 | Nobles et al. |
| 2002/0088189 A1 | 7/2002 | Honda |
| 2002/0124485 A1 | 9/2002 | Pulte |
| 2003/0023250 A1 | 1/2003 | Watschke |
| 2004/0243147 A1 | 12/2004 | Lipow |
| 2005/0043747 A1 | 2/2005 | Field et al. |
| 2005/0085857 A1 | 4/2005 | Peterson et al. |
| 2005/0119670 A1 | 6/2005 | Kerr |
| 2005/0234479 A1 | 10/2005 | Hatch et al. |
| 2005/0267529 A1 | 12/2005 | Crockett et al. |
| 2006/0069396 A1 | 3/2006 | Meade et al. |
| 2006/0075712 A1 | 4/2006 | Gilbert et al. |
| 2006/0196144 A1 | 9/2006 | Spek |
| 2006/0282088 A1 | 12/2006 | Ryan |
| 2007/0021755 A1 | 1/2007 | Almodovar |
| 2007/0060930 A1 | 3/2007 | Hamilton et al. |
| 2007/0060931 A1 | 3/2007 | Hamilton et al. |
| 2007/0062140 A1 | 3/2007 | Sillik |
| 2007/0088372 A1 | 4/2007 | Gellman et al. |
| 2007/0225735 A1 | 9/2007 | Stone et al. |
| 2007/0270885 A1 | 11/2007 | Weinert et al. |
| 2008/0243147 A1 | 10/2008 | Hamilton et al. |
| 2008/0249545 A1 | 10/2008 | Shikhman |
| 2009/0012538 A1 | 1/2009 | Saliman et al. |
| 2009/0024145 A1 | 1/2009 | Meade et al. |
| 2009/0157105 A1 | 6/2009 | Zung et al. |
| 2009/0292300 A1 | 11/2009 | Hamilton et al. |
| 2010/0010512 A1 | 1/2010 | Taylor et al. |
| 2010/0016868 A1 | 1/2010 | Kim |
| 2010/0030238 A1 | 2/2010 | Viola et al. |
| 2010/0152751 A1 | 6/2010 | Meade et al. |
| 2010/0268257 A1 | 10/2010 | Hamilton et al. |
| 2010/0280530 A1 | 11/2010 | Hashiba |
| 2011/0251627 A1 | 10/2011 | Hamilton et al. |
| 2011/0313433 A1 | 12/2011 | Woodard, Jr. et al. |
| 2012/0165837 A1 | 6/2012 | Belman et al. |
| 2012/0316580 A1 | 12/2012 | Belman et al. |
| 2013/0041388 A1 | 2/2013 | Lane et al. |
| 2013/0165954 A1 | 6/2013 | Dreyfuss et al. |
| 2013/0231687 A1 | 9/2013 | Laby et al. |
| 2013/0245646 A1 | 9/2013 | Lane et al. |
| 2013/0304096 A1 | 11/2013 | Nguyen et al. |
| 2014/0222036 A1 | 8/2014 | Hamilton et al. |
| 2014/0276988 A1 | 9/2014 | Tagge et al. |
| 2014/0276989 A1 | 9/2014 | Lane et al. |
| 2014/0288581 A1 | 9/2014 | Hamilton et al. |

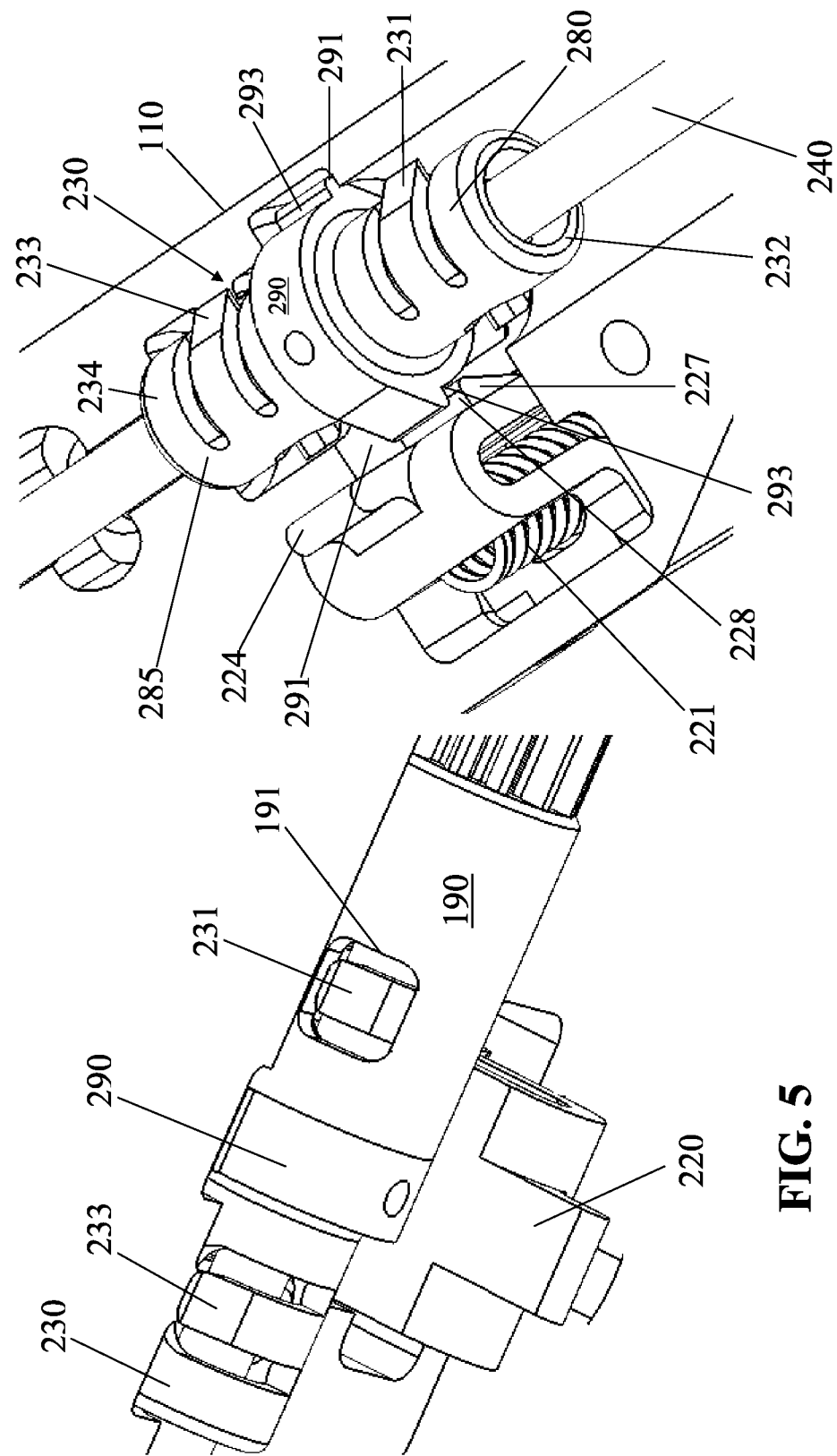

SYSTEMS AND METHODS FOR SUTURING TISSUE

CROSS-REFERENCE TO RELATED APPLICATION

The present application claims the benefit of and priority to U.S. patent application Ser. No. 61/994,890, filed May 17, 2014 and U.S. patent application Ser. No. 62/149,532, filed Apr. 18, 2015, each of which is hereby incorporated by reference in its entirety.

BACKGROUND

Needles and suture are used throughout the healthcare industry for indications such as wound and incision closure, securing catheters, and affixing implantable meshes, annuloplasty rings, and other medical apparatus. These sutures are used on the surface of the patient's skin as well as through laparoscopic, endoscopic, and surgical procedures. Because needles represent injury and illness risks to the user, there is a need to make needle usage safer without sacrificing ease of use, performance, and cost. A medical device that can be used to safely suture the tissue of a patient will be valuable to physicians, surgeons, nurses, physician assistants, military personnel, and other clinical and non-clinical users of suture.

SUMMARY

In one embodiment, a device for suturing tissue according to the present invention includes a handle including a housing having a distal end and an opposite proximal end and a suturing needle for advancing a suture through the tissue. The suturing needle has a first pointed end and an opposite second end. The device also includes a first needle gripper that is coupled to the housing and configured to both grasp and release the suturing needle. A second needle gripper is also coupled to the housing. The second needle gripper is configured to both grasp and release the suturing needle.

An actuator is coupled to the housing and is operatively coupled to: (a) a first linkage that pivots the second gripping gripper between a fully extended position and a retracted position relative to the housing; and (b) a second linkage that is operatively coupled to the first and second needle grippers and configured to alter a state of each of the first and second needle grippers to permit each respective needle gripper to either: (a) receive and grasp the suturing needle or (b) release the suturing needle. In accordance with one embodiment, the second linkage includes a one-way clutch that is operatively coupled to the actuator and is configured to synchronously alter the states of the first and second needle grippers to permit each respective needle gripper to either: (a) receive and grasp the suturing needle or (b) release the suturing needle.

The first linkage can include a plurality of gears that operatively couple the actuator to the second needle gripper such that motion of the actuator is translated into the second needle gripper rotating about a first pivot point between the fully extended position and a retracted positions. In addition, the second linkage can include an energy storage mechanism that is configured to store energy during an inward stroke of the actuator and release the stored energy during one stage of an outstroke of the actuator, whereby the release of the stored energy causes the states of the first and second needle grippers to be altered.

The device preferably includes additional features, such as a safety mechanism that shields the needle and a suture cutter.

BRIEF DESCRIPTION OF THE DRAWING FIGURES

FIG. 5 is another close-up of the windup mechanism along with a crankshaft assembly and a locking mechanism in the form of a pawl;

FIG. 6 is a perspective view of a crankshaft ratchet and the pawl in an engaged state;

DETAILED DESCRIPTION OF CERTAIN EMBODIMENTS

Figure 1A:
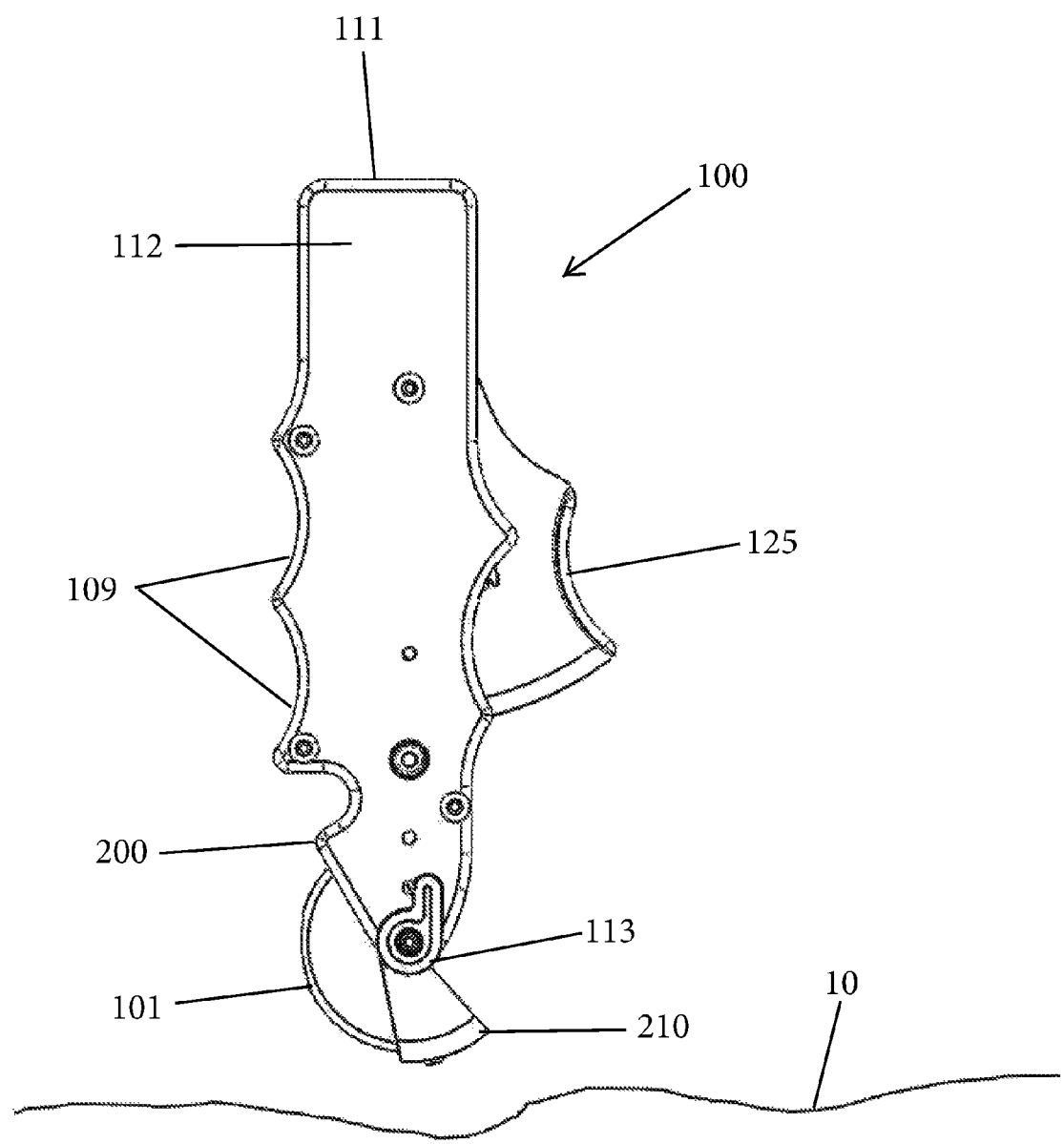
FIG. 1a is a side elevation view of a suturing device in a rest (packaged) position.

Disclosed herein are device concepts and methods for safely suturing tissue, skin, muscle, ligament, tendon and similar structures throughout the entire body. Healthcare workers need a safe method and device for closing wounds and incisions, approximating tissue, securing meshes and annuloplasty rings, securing catheters to a patient, and related functions. The current procedure typically consists of a user grasping an unprotected needle and suture with hemostats, a needle driver, forceps, or suturing device and then piercing the patient's tissue by utilizing hand, wrist, and device movements. In this scenario, the needle point is exposed to the user before, during, and after the procedure and provides risk for accidental needle stick injuries (NSI) to the user and procedural staff. These NSIs can transmit bloodborne pathogens such as hepatitis and HIV to the user and others from the patient and potentially cause illness or death. Users that are injured in this manner are required to report the injury, undergo diagnostic tests and begin receiving prophylactic treatment. They may also be required to take a leave of absence from work or continue indefinitely with a prescribed drug regimen.

A device according to one exemplary embodiment is a compact, light-weight handheld device that includes a needle and suture assembly, a mechanism for gripping and releasing the needle and suture assembly (a "needle transfer mechanism" or "needle shuttle mechanism"), safely capturing the needle assembly upon exit from the patient's tissue, and returning the needle to a position such that the process of delivering additional sutures to the patient can be repeated. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation (pivoting) suture delivery technique that is familiar to a user based on experience with other surgical techniques.

In a preferred embodiment, the device has the following definitive advantages over current art: Safety: The user cannot contact the point of the needle and is able to avoid accidental NSIs and the human and financial costs associated with those accidents. Performance: The device allows the user to reproduce the needle delivery motion that is currently used by healthcare workers. This improves the accuracy and integrity of the securement and reduces the trauma to the patient. Size: The device is sized and oriented for easy access to crowded and narrow regions of the patient's body such as the neck; Ease of Use: The device can be generally operated with one hand, by right-handed and left handed users, and multiple sutures are able to be secured to the patient through a minimal series of steps. Cost: The device is designed as a single use device that is economical and easy to manufacture. Versatility: The device is suitable for use within a hospital environment and any first aid setting. It can be utilized to secure nearly every type of catheter and to close wounds. In addition, it may be packaged within catheter and medical accessory sets or as a stand-alone device.

In one exemplary embodiment, the needle within this device can be returned to its starting point after it crosses the patient's tissue so that the device can be used to repeat the needle delivery process multiple times. At the conclusion of the process, the needle is safely retained by a mechanism within the device, which can then be safely disposed. In this embodiment, safety features are incorporated into the device such that the user cannot come into contact with the needle before, during, and after the procedure. In addition, an integral cutter is incorporated into the device in order that the suture can be cut by the user without the need for scissors or a scalpel. At the conclusion of each suture delivery, the safety features are automatically engaged and needle is safely shielded from the user. Additional elements within this embodiment include an integral cutter in order that the suture can be cut or trimmed by the user without the need for a separate scissors or scalpel.

Although it is contemplated as a single-use device, it is understood that slight alterations can be made to the design and materials that would allow said device to be resterilized, reloaded with an additional needle and suture, and reused. It may be further contemplated that the distally mounted needle has the ability to rotate relative to the handle and replicate the manual needle-driving motion of crossing tissue that is currently used in and outside the clinic. This is particularly useful in laparoscopic, endoscopic, and surgical procedures when the user's natural range of motion is compromised.

Looking again at the primary embodiment, the handle, which is comprised of one or more components such as a housing, actuator, and buttons, may be molded, cast or extruded from a variety of materials including but not limited to polymers or metals. Examples of polymers suitable for fabricating the handle are thermoplastic and thermosetting materials such as polystyrene, acrylic, polycarbonate, polyamide, polyester, polyetherimide, polysulfone, polylactic acid, polyvinylchloride, polyolefins, polyurethane, fluoropolymers, and copolymers and alloys thereof. These materials may be filled with glass or other useful reinforcing agents in order to enhance their mechanical properties. Suitable metals come from but are not limited to a group including titanium alloys and stainless steel. The selected materials must meet physical and mechanical performance requirements and be able to withstand sterilization methods employed within the medical device industry such as ethylene oxide or gamma irradiation. The handle design may be constructed to be linear and longitudinal, non-planar, angled, arcuate or a combination of these conformations.

The needle assembly generally consists of a suturing needle and a suture attached thereto. The suturing needle includes a distal pointed end suitable for piercing and crossing tissue and a blunt proximal end suitable for affixing a suture, and a body between the distal and proximal ends. The suturing needle can be fabricated in a variety of configurations from straight to curved and be monolithic or of a multi-part construction. The outer diameters of the needles can be round or non-round, tapered, or possesses features that assist in advancing and gripping the needle, i.e., flats, ribs, corners. Longitudinal ribs or recessions or other features found on the outer diameter of the needle may provide additional rigidity and enhance the needle's ability to effectively cross tissue. Needles are commonly made from stainless steel and related alloys but can be made from other metals, polymers and ceramic materials that are sufficiently rigid, capable of possessing and sustaining a functionally sharp distal point, and able to attach to suture. Traditionally, sutures are affixed to the proximal end of metal needles by swaging, crimping, knotting and adhesives. Suture attachment can also be configured such that the suture is affixed to the other regions of the needle, yet not the proximal terminus. This design variant provides additional freedom for suture management and gripping the needle in the device handle. In this configuration, attachment of the suture can be made by swaging, crimping, knotting, adhesives, etc. Coatings on the needle serve to enhance the lubricity of the needle and reduce tissue penetration forces.

The suture is the thread-like material that is used to treat internal and external wounds and incisions and to secure catheters or other components to patients. It comes in a variety of diameters, textures, forms, i.e., single strand or braided, and materials depending upon the desired properties and intended application. Sutures can be absorbable, i.e., collagen, polyglactin, polydioxanone, polyglycolide-lactide copolymers, or non-absorbable, i.e., silk, nylon, polyester, polypropylene, stainless steel. They can be treated with antimicrobial, bioabsorbable, hydrophilic or other functional additives. In addition, they can have surface features, e.g., barbs, that permit the suture to be drawn smoothly through tissue in one direction but snag the tissue when pulled in the opposite direction. This is advantageous when the user wants to temporarily or permanently approximate tissue without the need to tie a traditional knot.

The interfaces between the handle and the suturing needle/suture are generally referred to as the mechanisms or assemblies. These mechanisms serve to grasp, release, and shuttle the needle by manipulations to the handle by the user or by otherwise manipulating the device to cause the needle transfer. As will be appreciated from the detailed description below, there are a number of mechanical mechanisms that can be used to produce the desired movement of the suturing needle and more specifically, produce a reciprocal needle transfer action in which the suturing needle is initially held in one position within the mechanism and is then caused to be moved to another position within the mechanism to effectuate the suture needle passing into and through the tissue and then being subsequently extracted from the tissue. Further, after extraction, the mechanism is preferably designed to pass the suturing needle back from the needle capture/extraction position to the initial position at which the entire process can be repeated. Thus, one mechanism can be thought of as being a mechanism for cycling the suturing needle between different positions that result in the desired suturing action.

In addition, as used herein, the term "linkage" refers broadly to one or more parts that serve to link one part to another part. For example and as described herein, the actuator of the device is operatively connected to a number of other parts, assemblies or mechanisms by means of one or more linkages as set forth in greater detail herein.

It will thus be appreciated that a variety of mechanisms that are able to grasp, release, and shuttle the needle can be used. The mechanisms include but are not limited to rack and pinion, gearing, cams, ramps, screw bodies, springs, multiple-point gripping structures, i.e., 3-point, collets, drive belts, and rigid and flexible push rods to name a few. In instances, the suturing needle can comprise physical features that correspond to engagement features found within these mechanisms in order, for example, to increase grip strength. Some examples of these features are indentations, serrations, projections, faces, flats, undercuts, rings, and ports.

Moreover, the present device preferably includes a safety shield mechanism, which protects the user from the needle point before, during, and after the suturing procedure. The safety shield mechanism can exist in numerous forms in that any number of different mechanical arrangements can be used to accomplish the intended function. The safety shield mechanism can comprise single or multiple components, be biased to a safety-mode position and/or be user actuated, and/or have reversible or irreversible lock-out features. The safety shield mechanism can be configured, for example, as a slideable or rotatable cover, or as deflectable wing-like shields that obstruct user access to the needle point. Similar to the handle described above, the safety shield mechanism cans be made from a wide range of thermoplastics and thermosetting polymers; however, a transparent polymer may be more desired as it would provide the user with greater visibility of the needle and suturing site. Furthermore, the safety shield mechanism can be manufactured from metals, such as stainless steel, titanium, and titanium alloys including nickel-titanium, and configured as a wireform, mesh, grid, or strut. A spring or other force-resilient components can be incorporated in order to bias the safety apparatus into a safe position or to actuate multiple components that comprise the safety apparatus.

Referring to the lockout feature above, it will prevent the user from accidentally exposing the needle and obtaining an NSI. The lockout generally takes the form of a user-actuated button, lever, slide, or other similar means and a connecting element that couples the actuation means and the safety apparatus. The button causes the connecting element to lock and unlock the apparatus in a variety of ways. Examples of these means include tongue and groove, intermeshing gears, friction and interference fits, inclined planes, cantilever, and screws. In each of these methods, the connecting element restricts the movement of the apparatus, and therefore, the exposure of the needle until the user actuates the button to release the apparatus.

Finally, a suture cutter is preferably located within the device handle so that the user can trim knotted sutures and suture strands to length. One exemplary cutter can be a dynamic shearing apparatus, i.e., scissors or slideable blade(s), that requires the user to press or slide a button or manipulate an actuator having a different form, such as a knob or lever, in order to actuate the blade to cut the suture. To this end, the suture(s) can be positioned in a notch, slot, or hole located on the handle, and the actuation of the sharpened blade would cut the suture(s). Upon cutting the suture, a spring or similar biasing component would return the blade to its original position such that the cutting process can be repeated. The blade may traverse the suture cutting region with a linear, arcuate, or combination of these motions. Alternatively, the cutter can be a simple apparatus such as a static cutting blade located in a narrowing, crevice-like feature on the handle. In this configuration, the suture could be drawn across the sharp edge of the blade in order to cut it. Typical materials that are useful as cutting blades are stainless steel, carbon steel, and gemstones, such as diamond. For safety purposes, the user does not have direct access to the cutting blade; only suture is able to reach the blade via the suture cutter notch or hole. Beyond the safety advantage, the integral cutter would reduce or eliminate the need for the user to provide a separate pair of scissors for cutting or trimming suture during the procedure.

It will be appreciated that the above-described structures constitute exemplary parts of one suturing device according to the present invention and each of these structures is described in greater detail below. The foregoing discussion is thus a brief summary of suitable parts that can be present within the present suturing device; however, they are not to be considered to be limiting of the scope of the present invention. The make-up and operation of various exemplary suturing devices in accordance with the present invention are now described.

Referring to FIGS. 1a-1f, a suturing device 100 in accordance with a first embodiment includes a housing 110 that contains a number of the working components and allows a user to easily hold and use the suturing device 100. For example and as shown in the illustrated embodiment, the housing 110 can be in the form of an elongated handle that is formed of a first part 111 and a second part 114. The first and second parts 112, 114 are complementary to one another and include a means for attaching the two parts 112, 114 together to form an assembled handle 110 that can be easily grasped and manipulated by the user. For example, the first and second parts 112, 114 can be attached to one another by a mechanical attachment, such as by using fasteners (e.g., screws, bolts, etc.), by establishing a snap-fit between the two parts, or by another technique. The handle 110 not only houses many of the working components but also provides a means for the user to grasp the device 100 but also manipulate it in such a way to cause a needle 101 to be advanced into and through the tissue 10 and then exit the tissue 10.

Each of the first and second parts 112, 114 is generally hollow (e.g., a hollow shell) and therefore, when the two handle parts 112, 114 are attached to one another, they define a hollow interior handle space that receives and holds many of the working components of the device 100 as will be appreciated below. The first part 112 is an elongated handle part defined by a proximal end (upper end) 116 and a distal end (bottom end) 118 and similarly, the second part 114 is an elongated handle part that is defined by a proximal end (upper end) 117 and a distal end (bottom end) 119. The handle 110 can include ergonomic gripping regions/surfaces 109 suitable for both left and right-handed users to facilitate grasping of the device 100. As shown, these gripping regions 109 can be in the form of locally recessed and contoured portions of the handle 110 that locate and permit a user's thumb/fingers to grasp the exterior of the device 100. The gripping regions 109 can alternatively be defined by a modified exterior surface of the housing parts 112, 114 within local handle sections that allow the user to more easily grasp the handle. For example, the exterior surface of one or both of the handle parts 112, 114 can be a rough surface defined by surface features, such as a plurality of raised bumps or the like or can even be defined by a material that is different than the material of the handle and is applied thereto (e.g., a gripping surface member applied to the handle 110 by means of an adhesive or over-molding process or other suitable process). Additional examples of surface gripping features include but are not limited to loops, hooks and rings.

As shown in the figures and described in detail herein, the suturing device 100 is configured to move a curved suturing needle 101 in a controlled manner such that the suturing needle 101 is advanced into and through target tissue 10 and is then extracted from the tissue 10 to complete one suturing action and allow the user to tie off the suture element 102 itself. As mentioned herein, any number of different types of suturing needles 101 can be used with the device. In general, the suturing needle 101 includes a sharp distal end 103 for penetrating the tissue 10 and an opposite proximal end 104, which is typically a blunt end.

The device 100 also includes an actuator assembly 125 that is used to operate the device and to effectuate the controlled movement (shuttle action) of the suturing needle 101 and cause the suturing needle 101 to be driven into and then extracted from the tissue 10. The actuator assembly 125 includes an actuator body 126 that is accessible to the user and is manipulated by the user to cause controlled movement of the suturing needle 101. In the illustrated embodiment, the actuator body 126 extends from the side of the handle 110 and is accessible by the user. The actuator body 126 is operatively coupled to other parts of the actuator assembly 125 to cause the desired controlled movement as described herein below and in particular, causes needle transfer to effectuate the suturing action.

It will be appreciated that the illustrated actuator assembly 125 is merely one exemplary type of actuator that can be used in the present device to cause controlled movement of the suturing needle 101 and there are a number of other actuator assemblies that can be used for causing the needle 101 to be transferred (shuttled) in the manner described herein. For example, while the actuator body 126 is pivotably rotated by the user (e.g., as by pressing the body 126 into the hollow interior of the handle 110), other actuators suitable for use in the present invention can be activated by other techniques, such as pressing a button, rotating an actuator element, etc. In addition, the actuator body 126 is not limited to traveling within the hollow interior of the handle 110 but instead can travel long an outer surface of the handle 110. Thus, the actuator could be mounted on any number of the available surfaces on the device 100.

The needle transfer mechanism is comprised of two primary sub-mechanisms: a first gripping mechanism (first needle gripper or fixed clamp) 200 and a second gripping mechanism (second needle gripper or catch arm) 210. The first gripping mechanism 200 firmly holds the needle 101 and allows the user to penetrate tissue 10 and also to receive the needle 101 from the second gripping mechanism 210 in order to deliver additional sutures. The second gripping mechanism 210 serves to cover the sharp distal 103 end of the needle 101 while the device 100 is in its packaged and reset condition, and the second gripping mechanism 210 also serves to actively extract the needle 101 from tissue 10. The first gripping mechanism 200 is generally stationary within the handle 110, while the second gripping mechanism 210 is generally movable relative to the first gripping mechanism 200 and handle 110 to allow for transfer (shuttling) of the needle 101 between the first and second gripping mechanism 200, 210.

In the illustrated embodiment, the actuator body 126 extends from one side of the handle body and is operatively connected to a needle transfer mechanism, which as mentioned herein, is designed to controllably move the needle 101 from one operating position to another operating position and more specifically, to transfer the suturing needle 101 from one needle gripping mechanism 200, 210 to the other mechanism 200, 210 to allow the suturing needle 101 to be extracted from the tissue 10 once it passes therethrough.

Continuing with FIGS. 1a-1f, the general operation of the device 100 is depicted. Please note that not all features, i.e., suture cutters, depth controllers, safety apparatus, are shown in these figures. They are presented in separate figures and described in detail with reference to these other figures.

Figure 1B:
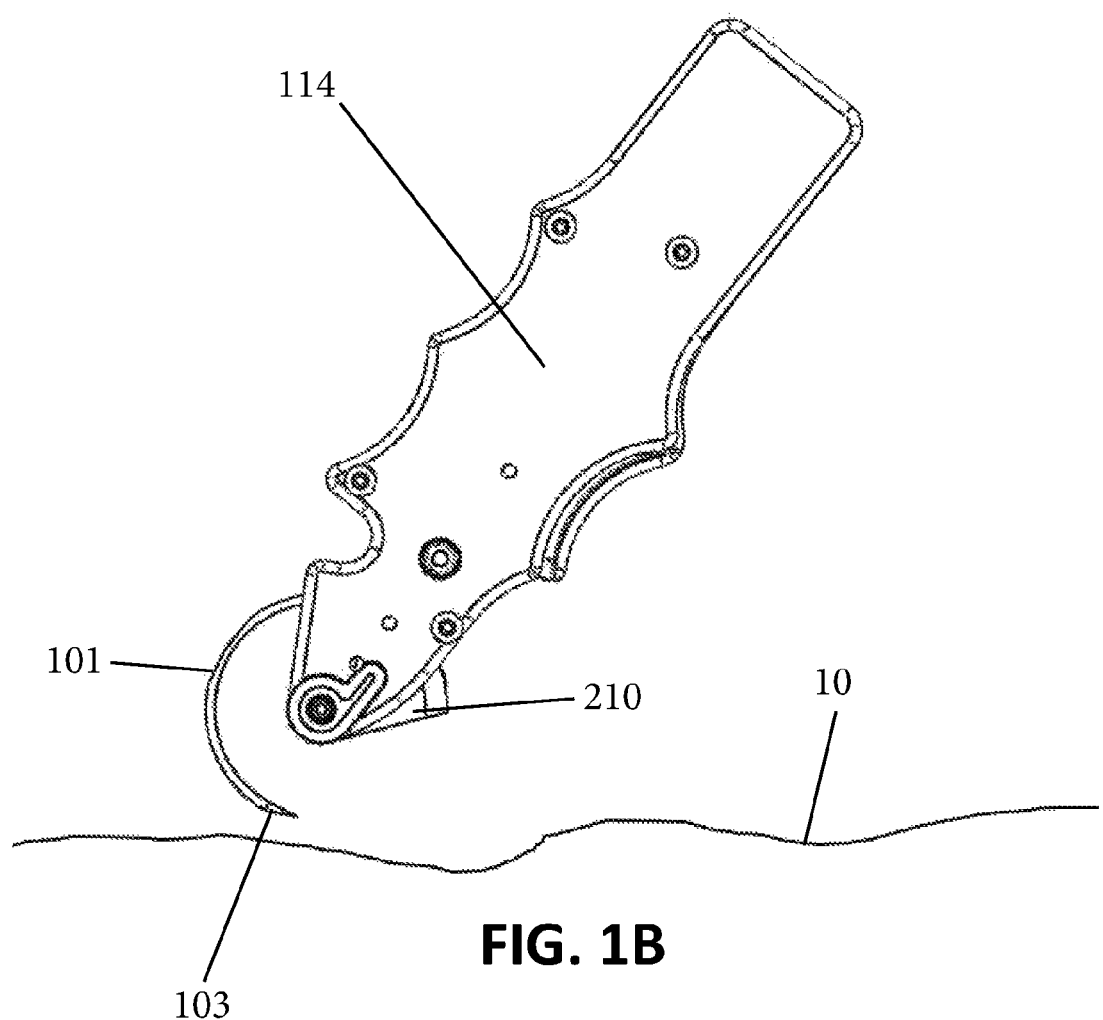
FIG. 1b is a side elevation view of the suturing device with a movable gripping mechanism in a retracted position after completion of an inward stroke of an actuator to expose a needle.
Figure 1C:
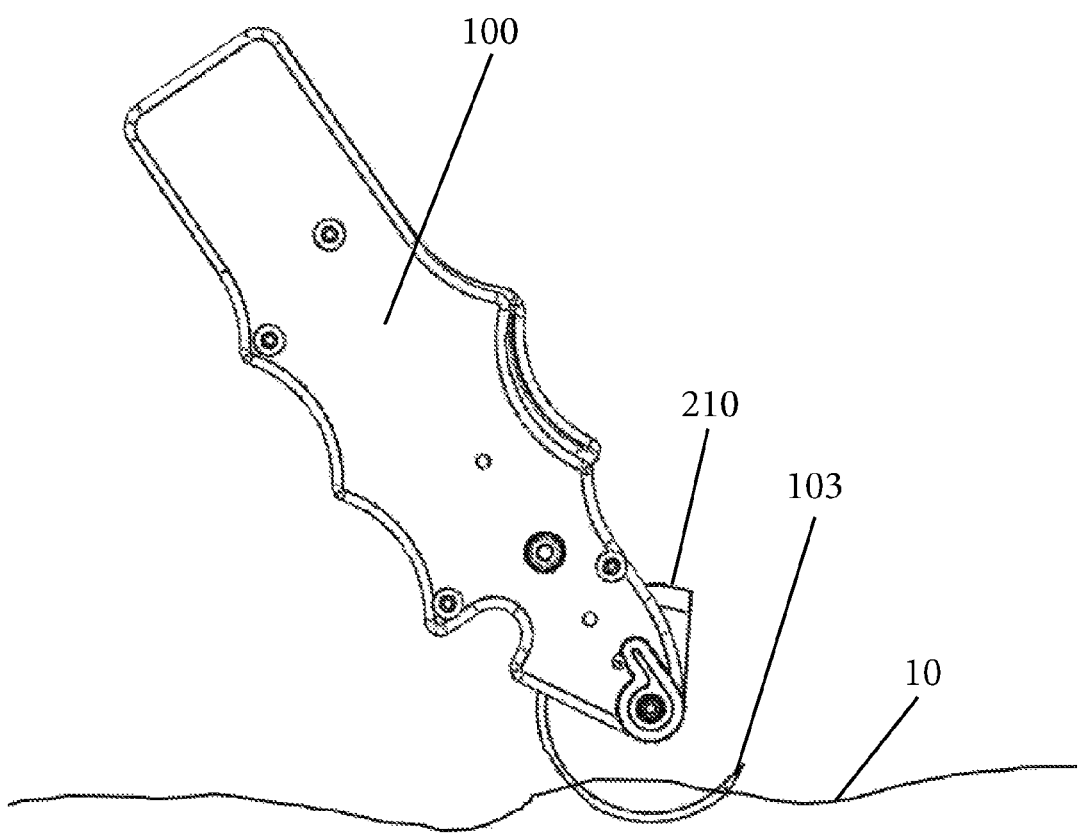
FIG. 1c is a side elevation view of the suturing device pivoted such that the needle penetrates and exits tissue.
Figure 1D:
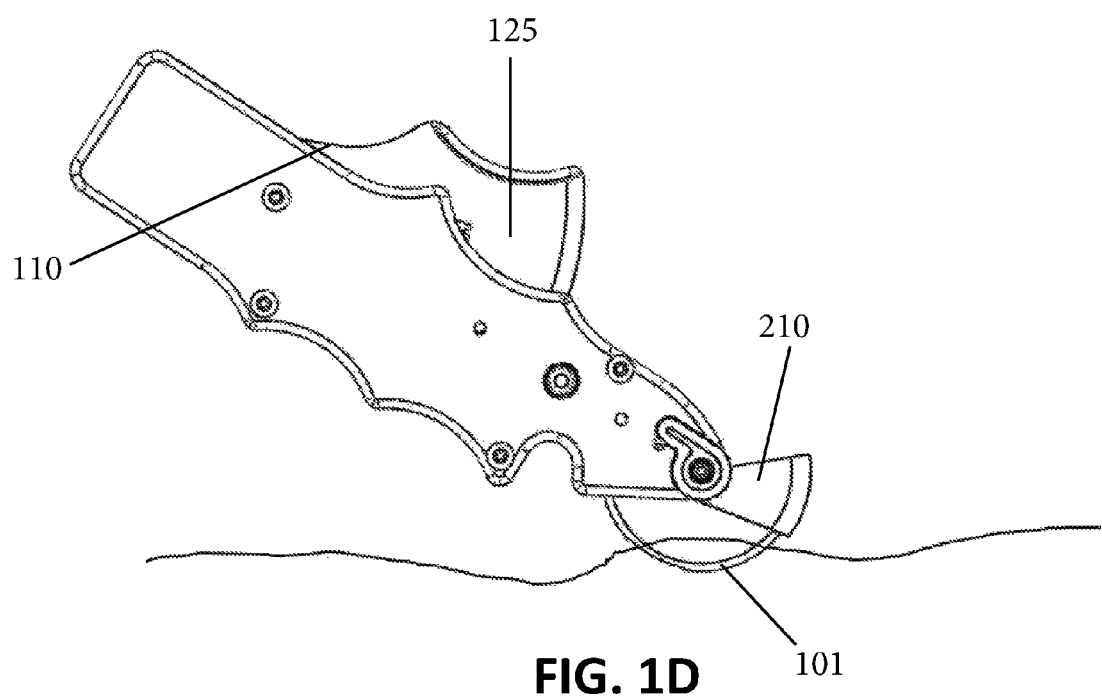
FIG. 1d is a side elevation view of the suturing device after the movable gripping mechanism returns to its extended state and grips the needle upon completion of an outstroke of the actuator.
Figure 1E:
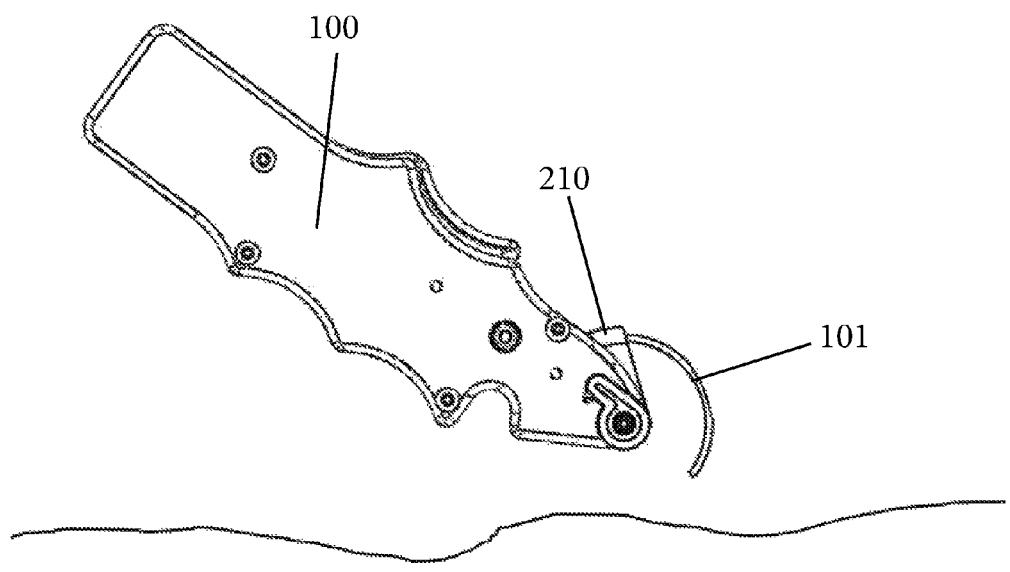
FIG. 1e is a side elevation view of the suturing device after a second inward stroke of the actuator is completed resulting in the needle being extracted from the tissue.
Figure 1F:
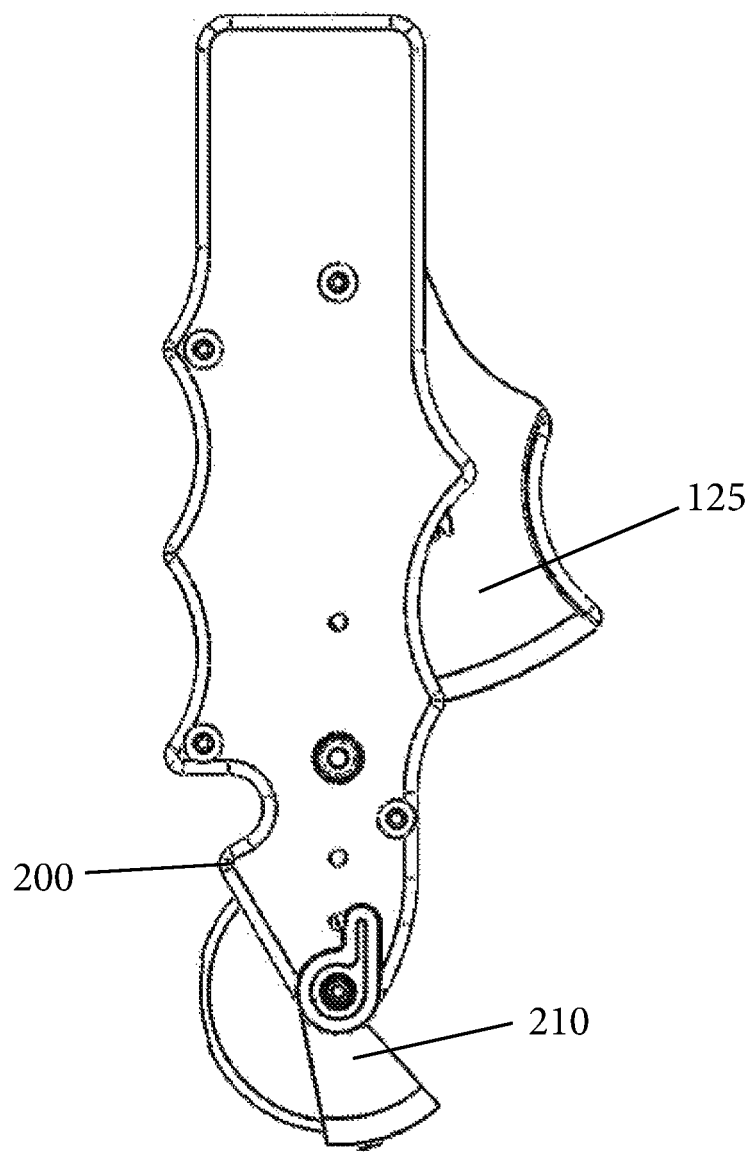
FIG. 1f is a side elevation view of the suturing device after an outstroke of the actuator is completed resulting in the needle being returned to the initial position.

FIG. 1a shows the device in its packaged condition (initial rest position) with the first gripping mechanism 200 having a firm grasp of the blunt end of the needle 101. The needle point 103 is covered by the second gripping mechanism 210 and is exposed when the user depresses the actuator 125 (inward stroke of the actuator 125 which results in a sweeping, non-linear motion of the actuator). The user can now penetrate the patient's tissue 10 with the needle 101 by orienting the handle 110 such that the needle point 103 is generally perpendicular to the tissue 10 as seen in FIG. 1b. Once the needle 101 is properly oriented, the user rotates his wrist such that the needle 101 penetrates and exits the tissue 10 as presented in FIG. 1c. When the needle 101 exits the tissue 10, a safety guard (not shown but illustrated in other figures) surrounds the needle point 103 and protects the user from injury. FIG. 1d depicts the second gripping mechanism 210 capturing the pointed end 103 of the needle 101 when the user releases the actuator assembly 125 (return stroke or out stroke of the actuator). With the needle 101 now gripped by the second gripping mechanism 210, the user can depress the actuator 125 (a second inward stroke) in order to actively extract the needle 101 from the tissue 10 as seen in FIG. 1e. Finally, in FIG. 1f the user releases the actuator 125 (a second return stroke or out stroke) and the needle 101 is rotated back to its origin, allowing the user to repeat the suture delivery process. The user may also activate the integral suture cutter (not shown) to cut the suture 102 to length or to trim the knotted suture.

In a preferred embodiment the device 100 is provided sterile in packaging, such as a blister pack. The device 100 comes out of the package in an at-rest condition where the needle 101 is gripped by the first gripping mechanism 200 near the distal end of the device 100, and the second gripping mechanism 210 is in its at-rest position enclosing the distal end of the needle 103, but not gripping the needle 101. The needle 101 features a length of suture from its mid-section.

The device 100 is constructed such that the actuator assembly 125 is operatively connected to a mechanism (linkage) that translates the movement of the actuator assembly 125 into controlled movement of the first and second gripping mechanisms 200, 210 in the manner described with reference to FIGS. 1a-1f.

Figure 1G:
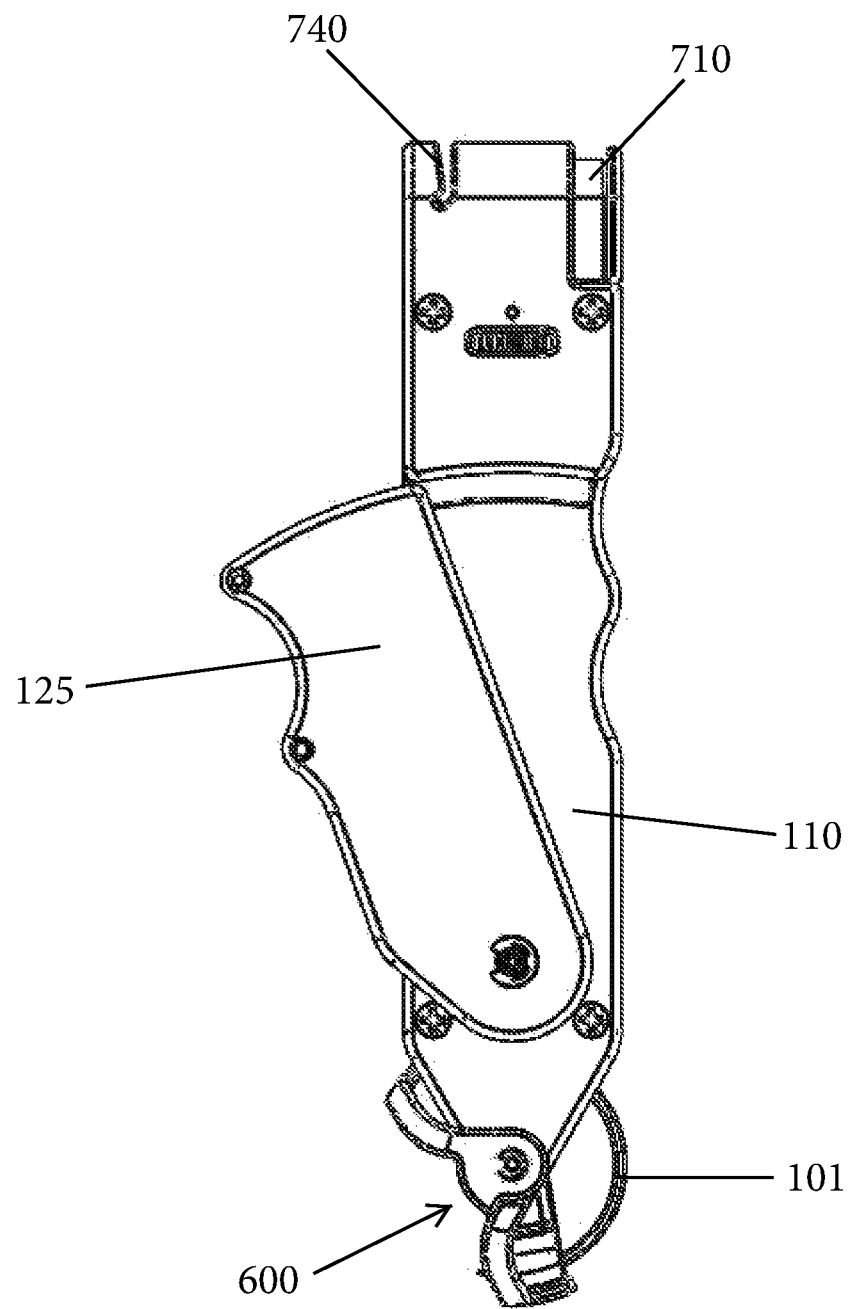
FIG. 1g is a side elevation view of a suturing device according to one embodiment showing one type of safety mechanism and needle grippers.
Figure 2:
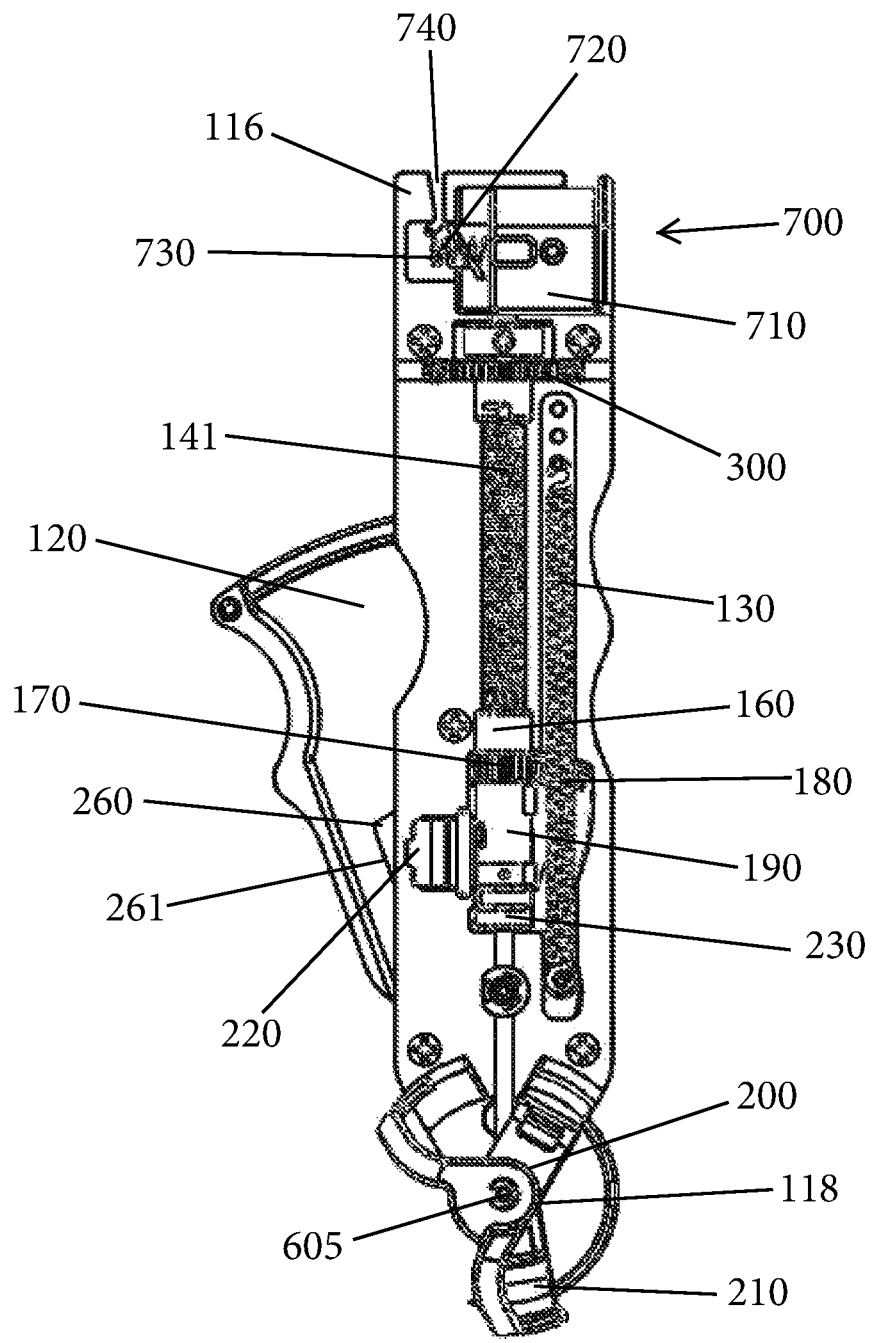
FIG. 2 is a side elevation view of one embodiment of the suturing device showing a gripping mechanism according to one embodiment.
Figure 3:
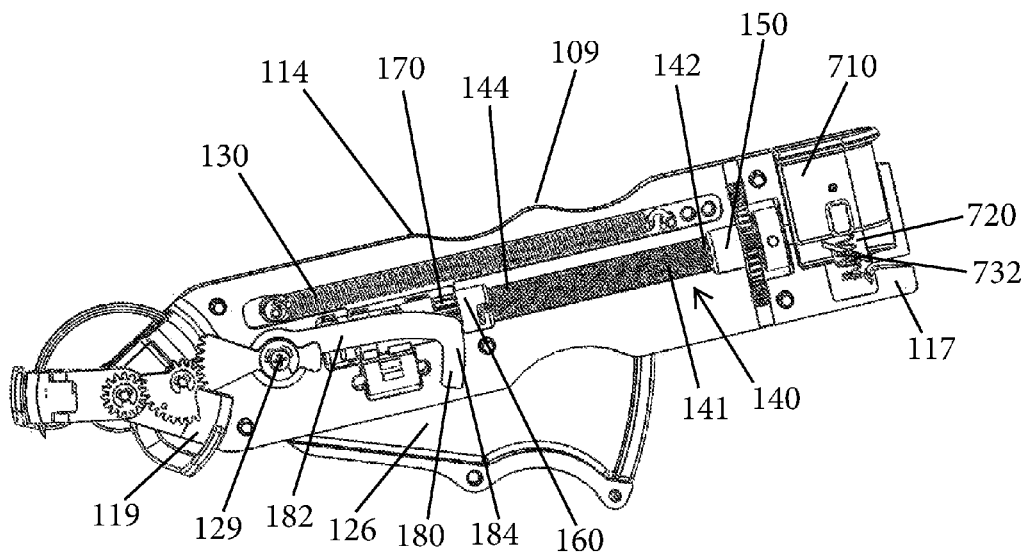
FIG. 3 is a side elevation view of a first side of the suturing device with one part of the housing removed to show the internal components of the actuator.

FIG. 1g shows device 100 according to one embodiment. FIGS. 2 and 3 show inner components and mechanisms that serve to controllably move the first and second gripping mechanisms 200, 210 in response to operation of the actuator assembly 125.

In one embodiment, the actuator 125 protrudes from the side of the housing 110 and swings (pivots) in an arcing motion from a first at-rest position to a mechanically limited, end-of-travel second position partially or fully inside or outside of the housing when squeezed by the user (i.e., an inward stroke of the actuator). A return spring 130 biases the actuator 125 toward the at-rest position and offers resistance to the user when squeezing. The return spring 130 is disposed within the hollow interior of the handle body. For example, the return spring 130 can be in the form of an elongated spring that has one end coupled to a first structure, such as the handle and an opposite end that is coupled to the actuator assembly 125. The return spring 130 is configured such that when an inwardly directed force is applied to the actuator body to cause the actuator body to pivot, the return spring 130 stores energy. After reaching the end of the inward stroke of the actuator, the energy stored in the return spring 130 is released and the actuator undergoes an out-stroke movement and returns to the initial rest position.

The actuator (assembly) 125 is connected to the second gripping mechanism 210 by mechanical means (gears, linkages, belts, cables or other means known to the art) such that when the actuator 125 moves from its at-rest position to its fully depressed position, the second gripping means 210 moves proportionally from its at-rest position to its fully retracted position. In this embodiment, the gear train connecting the actuator 125 and the second gripping mechanism 210 has approximately an 8:1 ratio; ~20 degree rotation of the actuator 125 results in a ~160 degree rotation of the second gripping mechanism 210. Of course, alternative gear count, size and ratios could be employed to accomplish the dynamic relationship between the actuator and second gripping means. In the at-rest position, the second gripping mechanism 210 can be thought of as being in a 6 o'clock position and in the fully retracted position, the second gripping mechanism 210 can be thought of as being in an approximately 1 o'clock position.

Figure 10:
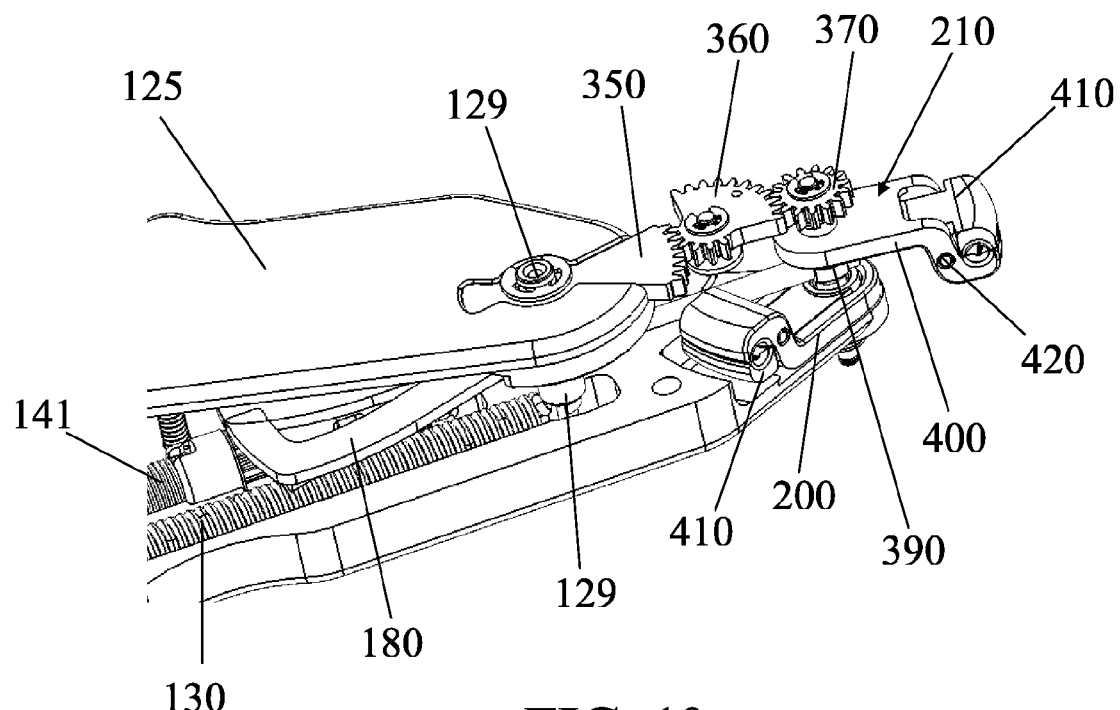
FIG. 10 is a perspective view of a first linkage (gear train) that connects the actuator to the second needle gripper.
Figure 11:
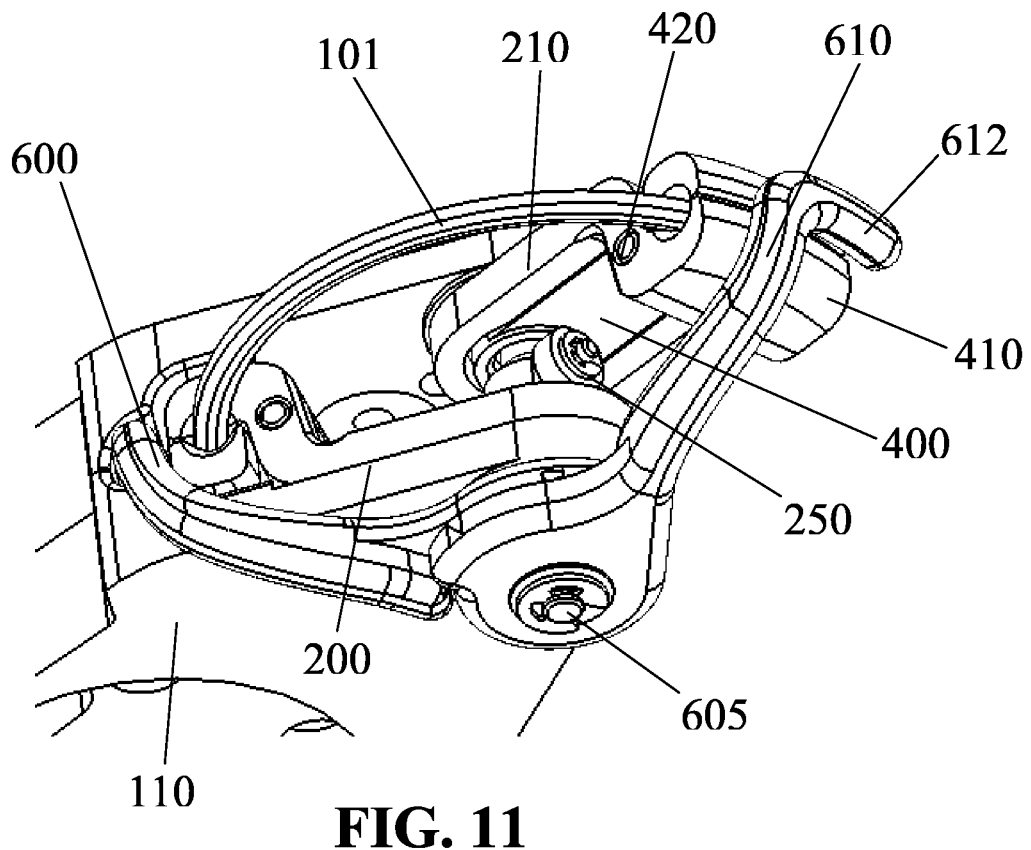
FIG. 11 is a perspective view of the distal end of the device showing a safety mechanism and the first and second needle grippers.

As shown in FIG. 10, the actuator 125 can be fixedly connected to a first gear (fan gear) 350 which moves in unison with the actuator 125 (and can be formed as an integral part thereof). The first gear 350 thus pivots about pivot 129 and includes teeth that face the second end 113 of the housing 110. The teeth of the first gear 350 mesh with a first set of teeth that belong to a second gear 360 that is pivotally mounted to the housing 110 and spaced from the actuator body 126. The second gear 360 also includes a second set of teeth that face the second end (distal end) 113 of the housing 110. The second gear 360 can be in the form of a reducer gear that can accomplish the approximately 8:1 ratio mentioned above. The second set of teeth of the reducer gear 360 mesh with teeth of a third gear 370 which pivots about an axle 390. The third gear 370 is fixedly coupled to the movable second gripping mechanism 210 and therefore, rotation of the third gear 370 results in rotation of the second gripping mechanism 210 and in this manner, the second gripping mechanism 210 can move across the range of motion shown in FIGS. 1a-f.

It will be appreciated that one function of the actuator 125 is to move the second gripping mechanism 210 in a pivoting manner. In both the inward stroke and the out stroke of the actuator 125, the motion of the actuator 125 is directly translated into pivoting of the second gripping mechanism 210 due to the action of gears 350, 360, 370 (which can be considered a linkage that operatively connects the actuator with the second gripping mechanism).

A second function of the actuator 125 will now be described an in particular, this second function deals with the alternating opening and closing of the first and second gripping mechanisms 200, 210 to facilitate the transfer of the needle 101 between the two mechanisms 200, 210 as a result of an energy transfer mechanism. In other words, the states (open or closed) of the first and second gripping mechanisms 200, 210 are altered by action of the actuator 125.

The actuator 125 is also connected (by gears or other means) to an energy storage device (member) 140. In one embodiment, this energy storage device 140 is a torsion spring 141.

It will be appreciated that the device 100 can utilize other mechanisms instead of the torsion spring 141 shown in the figures so long as these mechanisms provide the desired movements as described herein. For example, other embodiments can incorporate and be based on other kinds of springs, air compressing pistons, fly wheels, opposing magnets or any other energy storage means known to the art.

The torsion spring 141 is an elongated structure that has a first end 142 and an opposite second 144. Like the return spring 130, the torsion spring 141 is disposed within the hollow interior of the handle body and as shown, the return spring 130 and the torsion spring 141 can be disposed parallel to one another. The two springs 130, 141 can be located substantially side-by-side and they can partially overlap one another.

The torsion spring 141 can be coupled to a first mount (cap) (connector) 150 that is located at the first end 142 of the torsion spring 141 and a second mount (connector) 160 that is located at the second end of the torsion spring 141. The mount 150 is a fixed structure in that it does not rotate and serves as means for fixing the first end of the torsion spring 141 to the surrounding structure. Conversely, the second mount 160 moves with the torsion spring 141 and thus, both the torsion spring 141 and the second mount 160 are free to rotate in a first direction as the torsion spring stores energy and both are free to rotate in a second direction as the torsion spring 141 releases energy. As a result, when the second mount 160 is driven (rotated), as described below, the torsion spring 141 is likewise driven (rotated) in the same direction. Conversely, when the stored energy is released and the torsion spring 141 rotates and unwinds, the second mount 160 likewise rotates in the same direction.

The second mount 160 can thus be in the form of a circumferential structure that can be disposed about the second end of the torsion spring 141.

The internal energy transfer mechanism also includes a pinion gear 170 which is fixedly connected to the torsion spring 141 by means of the second mount 160. The pinion gear 170 is thus coupled to the second mount 160 such that the two parts move in unison. For example, rotation of the pinion gear 170 is translated into rotation of the second mount 160. The pinion gear 170 is driven by a rack 180 that is coupled to (but separate from) the actuator body 126 such that the actuator body 126 and rack 180 move together. The rack always remains coupled to the pinion gear 170. As shown in FIG. 3, both the rack 180 and the actuator body 126 can pivot (rotate) about a pivot point 129. On the inward stroke, the actuator 125 contacts and pushes the rack 180. A partial stroke and release causes the rack 180 to rotate the pinion 170 but then reverse due to the torsion spring 141. In a full inward stroke, the rack 180 remains with the pinion gear 170 when the pawl (described herein) lock the windup mechanism (described herein) in a cocked position. The return spring 130 alone creates the outstroke of the actuator 125. Since the rack 180 is not directly connected to the actuator body 126, the rack 180 stays in place in the cocked position during the out stroke of the actuator 125 until the stored energy of the windup mechanism is released at which time, the rack 180 returns to its first (initial) position.

The rack 180 includes an elongated arm portion 182 that is connected to the pivot point 129 and an engagement portion 184 which contains teeth that intimately mesh with the teeth of the pinion gear 170. As a result, when the rack 180 pivots about the pivot point 129, the engagement portion 184 moves in a sweeping action and this motion is directly translated into rotation of the pinion gear 170. This rotation of the pinion gear 170 is translated into rotation of the torsion spring 141 and depending upon the direction that the pinion gear 170 is rotated, the torsion spring 141 will either windup and store energy or wind-down and release stored energy. In particular, the pinion gear 170 is wound-up one half turn by the rack 180 when the actuator 125 is depressed fully (a full inward stroke of the actuator), and is configured to hold the stored energy of this half turn when the actuator 125 reaches its fully depressed position.

It will be appreciated that the rack 180 alternatively can be arc shaped and not have an L-shape as shown provided that the rack 180 is supported. In addition, the rack 180 also does not have to share a pivot with the actuator 125.

Looking at FIGS. 2-5, the energy transfer mechanism also includes a windup ratchet 190 that is a generally hollow body that includes a first end 192 and an opposite second end 194, with the first end 192 facing the pinion gear 170. As described herein, the windup ratchet 190 is disposed within the housing 110 in such a way that it has controlled rotation therein during the inward stroke and a subsequent out stroke.

As used herein, the "windup mechanism" comprises the torsion spring 141, the mounts 150, 160, the pinion 170 and the windup ratchet 190.

Figure 4:
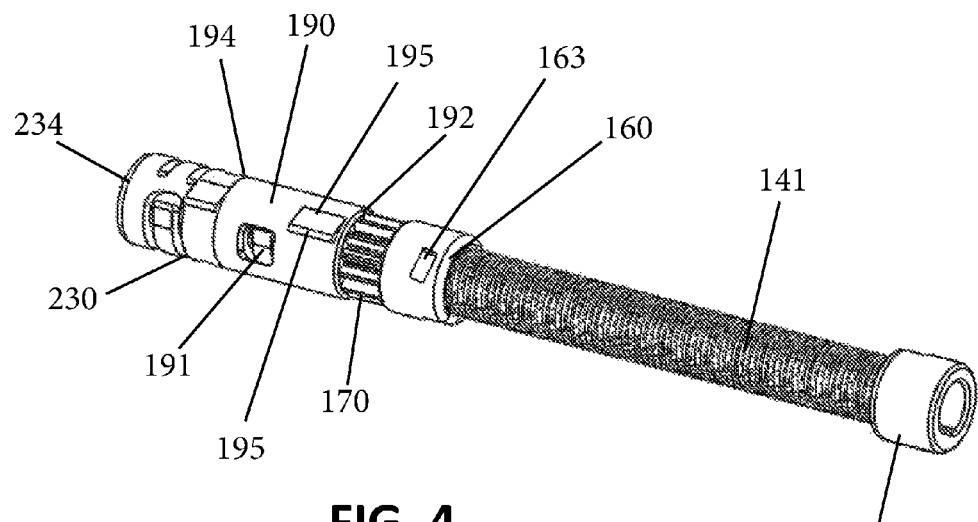
FIG. 4 is a close-up of a windup mechanism that is part of the actuator.

The windup ratchet 190 includes a first window (opening) 191 and a second window (opening) that is spaced from the first window 191. The first and second windows 191 can be formed about 180 degrees from one another. The windup ratchet 190 includes at least one protrusion 195 that extends outwardly from the outer surface of the windup ratchet 190. As shown in FIG. 4, each protrusion (tab) 195 can be located adjacent one of the windows.

In one embodiment, as described herein, the protrusion 195 acts as mechanism for restricting movement (rotation) of the windup ratchet in one direction. More specifically, the housing 110 can include an interference (a wall) that stops and limits the rotation of the windup ratchet 190 when the protrusion 195 makes contact (seats against) such wall or other part. The windup ratchet 190 is configured to rotate 180 degrees and thus, the protrusion 195 and interference are formed such that the windup ratchet 190 is prevented from being rotated more than 180 degrees. As described herein, other alternative 180 degree mechanisms can be incorporated into the device including element 163 which is discussed herein. In particular, a stop can be incorporated into any one of the components that make up the windup mechanism to limit its travel to 180 degrees (the actuator stroke distance limits the instroke rotation angle of the windup assembly and the protrusion 163 limits the rotation angle of the windup assembly during the outstroke).

It will be understood that the cap 160, the pinion gear 170 and the windup ratchet 190 can be formed as single part as opposed to three separate parts.

In one embodiment, the fixed coupling between the windup ratchet 190 and the pinion gear 170 allows the windup ratchet 190 to rotate 180 degrees as the rack 180 is moved by operation of the actuator 125. As just mentioned, the protrusion 195 on the windup ratchet 190 engage the housing 110 in order to limit the rotation of the windup ratchet 190 to 180 degrees of movement. This stop (e.g., protrusion 195) serves to stop the windup mechanism after the energy in the windup mechanism is released. As described herein, a pawl 220 additionally controls the rotation and timing of the rotation of the windup ratchet 190. The stop/interference point can be thought of as being a zero point of the pinion rotation and the pawl engagement (described herein) is the 180 degree point.

In addition, the windup ratchet 190 also rotationally engages a crankshaft ratchet 230. The crankshaft ratchet 230 is fixedly attached to an elongate crankshaft 240. Similar to the windup ratchet 190, the crankshaft ratchet 230 is a hollow structure that includes a first end 232 and an opposite second end 234. As shown in the figures, the crankshaft ratchet 230 is disposed along the length of the crankshaft 240 such that a first portion of the crankshaft 240 extends outwardly from the first end 232 and a second portion of the crankshaft 240 extends outwardly from the second end 234.

As shown in the figures, the crankshaft ratchet 230 includes a first end portion 280, a second end portion 285 and a center portion 290 that is located between the first and second end portions 280, 285. Each of the first end portion 280, second end portion 285, and center portion 290 thus extends circumferentially about the crankshaft 240. The first end portion 280 faces the pinion gear, while the second end portion faces the gripping mechanisms 200, 210. The first end portion 280 has a pair of first flexible tabs 231 that can be in the form of flexible fingers that each has a beveled free end. The flexible tabs 231 can be oriented approximately 180 degrees apart. The second end portion 285 can be a mirror image of the first end portion 280 and includes a pair of second flexible tabs 233 that can be in the form of flexible fingers that each has a beveled free end.

The center portion 290 includes a pair of locking tabs 291 that are oriented approximately 180 degrees apart from one another. The locking tabs 291 have a beveled appearance that terminates in a locking surface 293. The locking tabs 291 face in opposite directions in that the locking surface 293 of one locking tab 291 faces in one direction, while the locking surface 293 of the other locking tab 291 face in an opposite direction as shown.

The first flexible tabs 231 are configured to selectively engage the first and second windows formed in the windup ratchet 190 to selectively interlock the crankshaft ratchet 230 to the windup ratchet 190 during operation of the actuator cycle(s). As described herein, when the crankshaft ratchet 230 is coupled to (interlocked with) the windup ratchet 190, the rotation of the windup ratchet 190 is translated to the crankshaft ratchet 230 and since the crankshaft 240 is attached to the crankshaft ratchet 230, the crankshaft 240 itself rotates in unison with the other coupled parts. As described herein, the rotation of the crankshaft 240 controls the operation of one aspect of the first and second gripping mechanisms 200, 210 to allow for the shuttle action of the needle 101 between the two gripping mechanisms 200, 210.

In the initial position of the device, the flexible tabs 231 are disposed within windows 191 of the windup ratchet 190. During a first inward stroke of the actuator 125, the windup ratchet 190 is rotated in a first direction by the motion of the actuator 125 as described herein and this results, in the windows 191 of the windup ratchet 190 moving relative to the first flexible tabs 231 of the crankshaft ratchet 230 (which remains fixed and stationary during the inward stroke due to a stop formed as part thereof (e.g., tab 233)). As the windup ratchet 190 rotates, the tabs 231 flex and are disengaged from the respective windows 191 due to the cam surfaces (structures) of the tabs 231. At the end of the first inward stroke, the tabs 231 are placed in registration with windows 191 (i.e., the opposite windows compared to the starting point) of the windup ratchet 190 and the compressed tabs 231 spring into the windows 191, thereby releasably interlocking the two ratchets 190 to one another (See FIG. 5).

Figure 8:
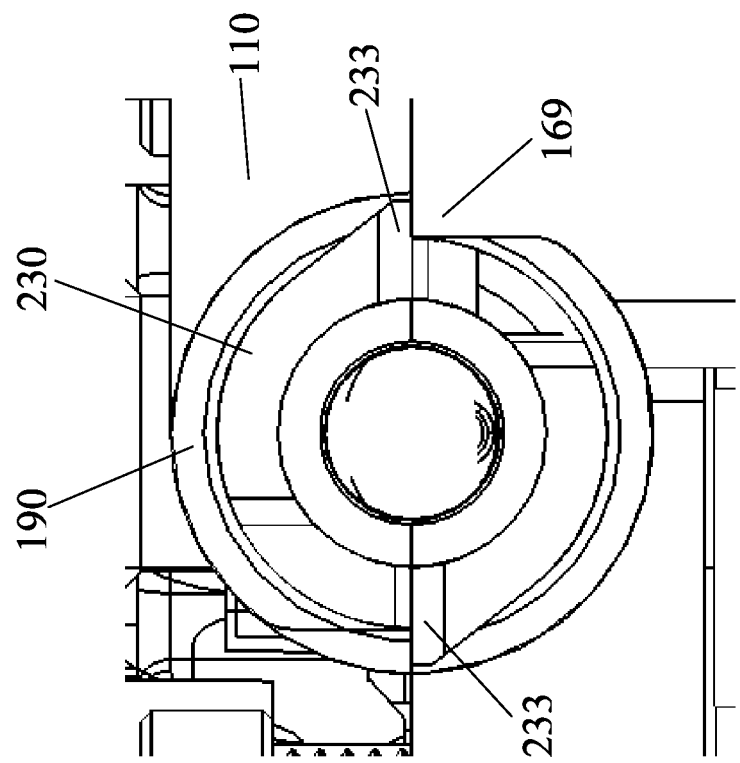
FIG. 8 is a cross-sectional view of the combined crankshaft ratchet and windup ratchet showing an anti-reverse feature of the crankshaft ratchet.

As described below, the pawl 220 is unlatched during the initial rest position of the device and becomes latched during an inward stroke and this prevents the entire now linked assembly from moving (rotating). In addition, as shown in FIG. 8, during the inward stroke of the actuator 125, the tabs 233 serve as an anti-reverse feature that prevents rotation of the crankshaft ratchet 230 during the inward stroke of the actuator 125. This results when the tabs 233 contact a stop 169 that is part of the housing 110 as shown in FIG. 8.

When the actuator 125 is released and the actuator 125 undergoes its out stroke action, the actuator 125 is returned to its initial rest position by means of the return spring 130. During almost the entire outstroke action, the releasably coupled windup ratchet 190 and crankshaft ratchet 230 do not move (due to the stops (i.e., tabs 233) and other features described herein) until the pawl 220 is tripped as described herein at which time the windup mechanism becomes released from the pawl 220 and spins (rotates) 180 degrees in the opposite second direction due to the release of the stored energy of the torsion spring 141. It will be understood and is described herein that during the out stroke, the movable second gripping mechanism 210 moves.

When the user performs the next second inward stroke action of the actuator 125, the process repeats and the tabs 231 are released from the windows 191 due to the rotation of the windup ratchet 190 and the structure (cam edge) of the tabs 231. The process repeats and the windup mechanism stores energy and the windup ratchet 190 rotates about 180 degrees before tabs 231 reengages windows 191, thereby fixedly (yet releasably) coupling the windup ratchet 190 to the crankshaft ratchet 230 as described above.

Figure 7:
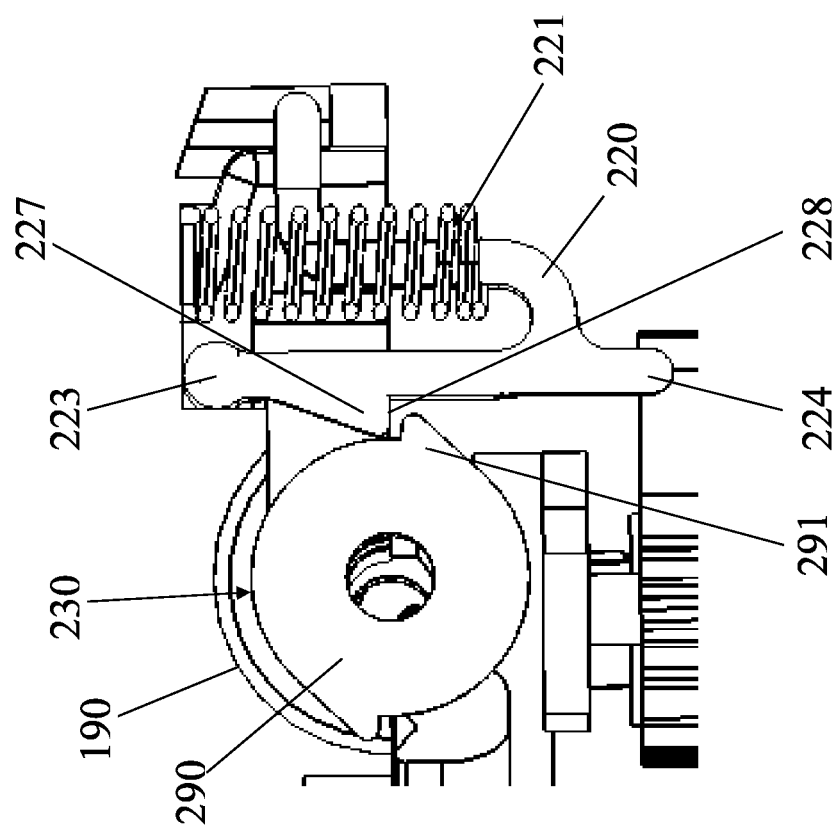
FIG. 7 is a cross-sectional view of the crankshaft ratchet and pawl in the engaged state.

As best shown in FIGS. 6-7, the pawl 220 is disposed within the housing 110 and has a degree of movement within the housing 110. More particularly, the pawl 220 pivots about a pivot 223 as shown in FIG. 8. The pivot 223 is located at a first end of the pawl 220. The pawl 220 is biased by a biasing member 221, such as a spring, that applies a biasing force to the pawl 220. The spring 221 can be oriented horizontal or vertical and biases the pawl 220 into the crankshaft ratchet 230 for maintaining the crankshaft ratchet 230 and crankshaft 240 in a held position (no rotation) (See FIG. 7).

The pawl 220 also includes a trip lever 224 that is in the form of a protrusion that extends outwardly from the pawl 220 at a second end opposite the first end. The trip lever 224 can have a rounded shape as shown. The pawl 220 also includes a step or locking member 227 that has a locking surface (a shoulder) 228 that is configured to selectively engage one of the locking tabs 291 formed in the center portion 290 of the crankshaft ratchet 230. More particularly, the step 227 serves to hold the windup mechanism in a cocked position. This windup mechanism and the crankshaft components can be thought of as being a linkage that operatively couples the actuator to the first and second gripping mechanisms for controllably moving each of the gripping mechanism between open and closed positions. As described herein, this cocked position is maintained until the trip lever 224 of the pawl 220 is actuated (tripped) by coming into contact with a trigger which in the case of the illustrated embodiment is a wall that is part of the actuator 125 of the suturing device 100. In particular, the actuator 125 includes a recess 260 formed therein. One end of the recess 260 is defined by a wall (ledge) 261 which acts as a trip for the pawl 220. As understood, the actuator 125 is pivoting and thus the recess 260 and the wall 261 are continuously moving during an inward stroke and an out stroke of the actuator 125. At the same time, the pawl 220 is pivotally mounted to the housing and the trip lever 224 is disposed within the recess 260. Thus, during the out stroke of the actuator 125, when the trip lever 224 contacts the ledge 261, the pawl 220 pivots about pivot 223, thereby causing the locking member 227 to disengage from the locking tab 291 of the crankshaft ratchet 230. In particular, up until the final stage of the out stroke (e.g., during approximately the last 5% of movement of the actuator 125), the pawl 125 is engaged to the crankshaft ratchet 230; however, during this final stage, the pawl 220 is tripped as described herein and the pawl 220 disengages from the crankshaft ratchet 230, thereby allowing the crankshaft ratchet 230 to rotate as the stored energy is released.

Since the pawl 220 is functioning to hold the crankshaft ratchet 230 in its wound up (ready to fire) position, once the pawl 220 is released from the crankshaft ratchet 230, the crankshaft ratchet 230 releases its stored energy by rotating over a defined degree of travel (e.g., about 180 degrees). As will be understood, the crankshaft ratchet 230 rotates due to the release of energy stored by the torsion spring 141 since the crankshaft ratchet 230 is coupled thereto by its engagement with the windup ratchet 190 (due to flexible tabs 231 being disposed in the windows 191). When the windup mechanism is fired and releases its energy, the anti-reverse tabs 233 flex to allow rotation of the crankshaft ratchet 230 as will be appreciated in view of FIG. 8. More specifically, in FIG. 8, the crankshaft ratchet 230 rotates in the second direction (e.g., counterclockwise in FIG. 8) when the pawl 220 is tripped and the mechanism is fired and the cam structure and flexing properties of the tab 233 allows for such rotation in this second direction for the controlled 180 degrees. Conversely, during the inward stroke, movement of the crankshaft ratchet 230 in the first direction (e.g., clockwise direction in FIG. 8) is restricted by the anti-reverse tab 233 contacting the stop 169 of the housing 110. After the firing of the windup mechanism, the tab 233 in FIG. 8 that is shown being free of the stop 169 then assumes an engaged state with the stop 169.

In one rotational direction (actuator depressing action in the illustrated embodiment), the windup ratchet 190 slips past the crankshaft ratchet 230, whereas in the opposite rotational direction, the windup ratchet 190 engages and rotates the crankshaft ratchet 230 during its rotation (near the end of the actuator return stroke in the illustrated embodiment). This one way clutch, comprised of the windup ratchet 190, crankshaft ratchet 230 and pawl 220, is configured with synchronous, compliant and non-compliant protrusions and grooves, which control the rotation and timing of these components and the energy storage/release mechanism as described herein. For those skilled in the art, it is understood that many forms of one-way clutches (rotors, pads, drums, diaphragm springs, pressure plates, hydraulic, centrifugal, electromagnetic, etc.) can be used to store and release energy in this or a similar design.

A rotatable, concentric bearing 250 is affixed to a distal, eccentric portion of the crankshaft 240 and engages the first and second gripping mechanisms 200, 210 in order to create two synchronous clamping states (needle grip and needle release) as the crankshaft 240 rotates in 180 degree increments. By mounting the bearing 250 in an eccentric manner, the bearing 250, as it rotates, can contact one of the first and second gripping mechanisms 200, 210 and then as the bearing 250 continues to rotate, it contacts the other of the first and second gripping mechanisms 200, 210 (in an alternative embodiment, the bearing 250 could be designed to contact both mechanism 200, 210 at once in a disproportionate manner in that during the 0 and 180 degree states of the device, the load can be distributed disproportionately (e.g. 99/1) between the two mechanism 200, 210. As will be described below, the contact and motion of the bearing 250 against a portion of each of the first and second gripping mechanisms 200, 210 causes the respective gripping mechanism to move between a first clamping state (needle grip state) and a second clamping state (needle release state).

Eccentricity of the crankshaft 240 can be achieved with a concentric bearing and eccentric shaft or a concentric shaft and eccentric bearing, a single component featuring a shaft and bearing surface, a rotatable or fixed bearing, a bearing that is round or flat-edged, or any other obvious cammed shaft components and designs. In an alternative embodiment, there could be multiple bearings acting upon the respective gripping mechanisms 200, 210 instead of one central bearing (i.e., the concentric bearing 250). Also, staged bearings that work in tandem to first move the bearing 250 and gripping mechanisms 200, 210 nearly into its final position and then to use additional bearings to move the gripping mechanisms 200, 210 into its final position can be employed.

Figure 9:
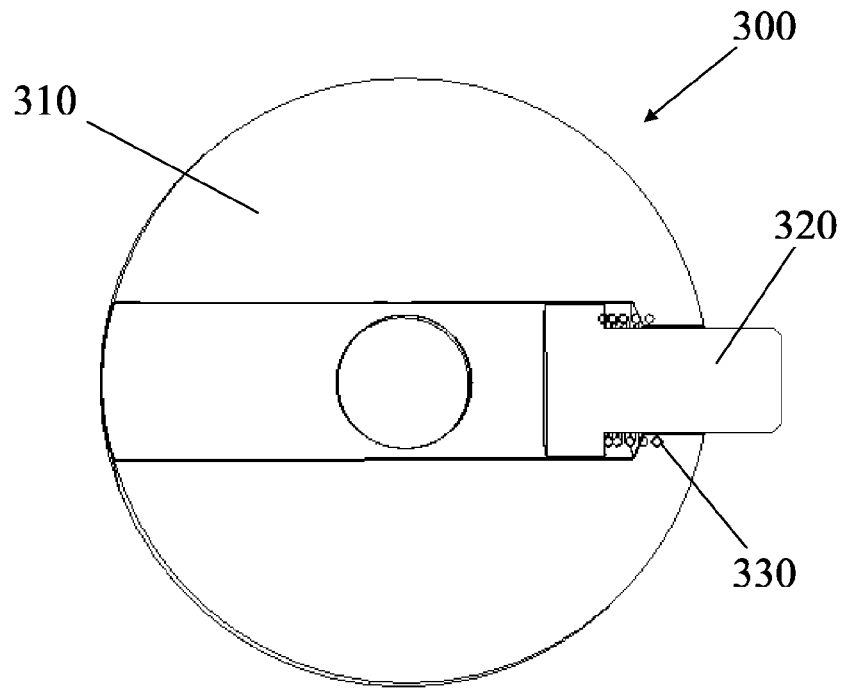
FIG. 9 is a cross-sectional view of a mechanism to stop rotation of a crankshaft after it has rotated a predetermined number of degrees.

The device 100 also can include a mechanism to limit (restrict) the rotation of the crankshaft 240 to 180 degrees (to keep the crankshaft in phase) during one actuator cycle of the actuator (similar to the other mechanisms described herein to limit rotation of the active parts to about 180 degrees during one actuator stroke). One type of mechanism is shown in FIGS. 2 and 9 and comprises an inertia wheel assembly 300 is connected to the crankshaft 240 for the assistive purpose of limiting the crankshaft's rotation to 180 degrees. The assembly 300 in this embodiment is generally comprised of a disc 310, a pin 320, and a biasing member 330 (spring, elastic, resilient foam). In its simplest form, the inertia wheel disc 310 is rigidly attached to the crankshaft 240 and the pin 320 is biased by the biasing member 330 in retracted (at-rest) position. When the crankshaft 240 rotates rapidly, e.g., as the stored windup energy is released as described herein, the centrifugal force exacted onto the pin 320 causes the pin 320 to project beyond an outer surface of the disc 310 and to contact the housing 110 at one of two locations, which are separated by 180 degrees of rotation. This interference between the extended pin 320 and the housing 110 acts as a stop to limit the degree of travel of the crankshaft 240. The pin 320 then retracts when the inertia wheel (disc) 310 stops rotating.

FIG. 4 also illustrates that the part 160 can also include a pin 163 (e.g., a spring mount pin) that acts as a hard stop for the windup mechanism after the windup mechanism is tripped (i.e., by disengagement of trip lever 224 of pawl 220). The pin 163 contacts the housing 110 and acts as stop for the windup mechanism (as an alternative to the use of tab 195). It will thus be understood that while FIG. 4 shows both tabs 195 and pin or protrusion 163, in practice, only one of these features would be provided.

As mentioned, the crankshaft ratchet 230 also engages pawl 220, which retains the ratchets 190, 230 in an energy stored state and then is later tripped by a feature (i.e., ledge 261 that is part of recess 260 formed in the actuator 125—see FIG. 2) when the actuator 125 nears the completion of its return stroke (out stroke). It will be appreciated that other features in the actuator, gripping means, housing, or other appropriate element may be used to trip the pawl. This tripping action of the pawl 220 (during the final stage of the outstroke of the actuator) releases the stored energy in the torsion spring 141, which instantaneously rotates the windup ratchet 190, crankshaft ratchet 230, crankshaft 240, and bearing 250 180 degrees as a result of the coupling between these parts, as described herein, and this rotation of the bearing 250 activates one of the first and second gripping mechanisms 200, 210, while deactivating the other of the first and second gripping mechanisms 200, 210. This action effectively holds the needle 101 rigidly in one of the first and second gripping mechanisms 200, 210, while the other of the first and second gripping mechanisms 200, 210 releases the needle 101, thus, enabling the transfer of the needle between the first and second gripping mechanisms 200, 210.

Figure 12:
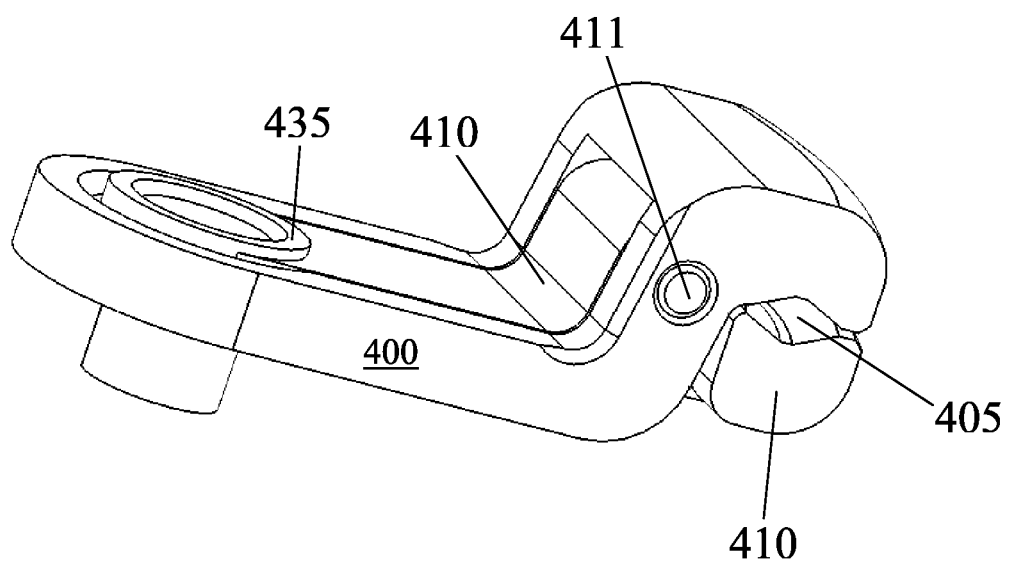
FIG. 12 is a perspective view of one needle gripper.
Figure 13:
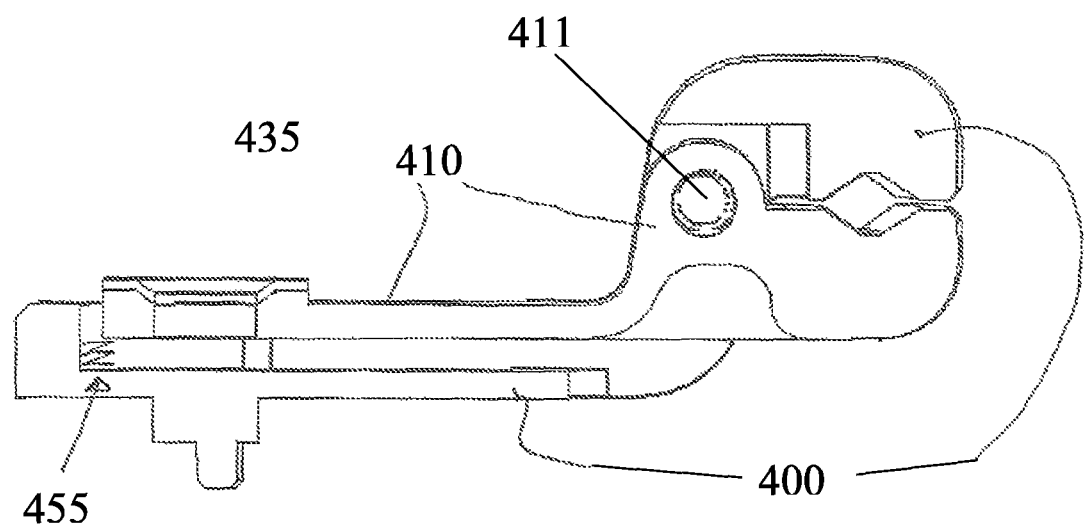
FIG. 13 is a cross-sectional view of one needle gripper.

As mentioned, there are two similar gripping mechanisms (first and second needle grippers) 200, 210 in the illustrated embodiment that grip the needle 101 in essentially the same manner. Each of the gripping mechanisms 200, 210 can be comprised of a stationary (fixed) gripper (jaw) 400, a movable gripper (jaw) 410, and a hinge pin 420 that pivotally couples the movable jaw 410 to the fixed jaw 400 and allows the movable jaw 410 to pivot about point 411. As shown in FIGS. 12 and 13, the movable jaw 410 can function as a lever in that when a force is applied to one end of the movable gripper 410, the other end of the movable jaw 410 pivots about point 411 allowing the needle gripper 200, 210 to close. The movable jaw (lever or pin) 410 is contacted by the bearing 250 and rotation of the bearing 250 selectively applies a force to the movable jaw 410 (such as pressing down on one end of the lever) resulting in movement of the movable jaw 410. In the illustrated embodiment, the bearing 250 contacts a boss 435 that is part of the movable jaw 410 and the rotation of the bearing 250 (as a result of the crankshaft 240 being driven) results in the jaw 410 being pushed down at one end causing the opposite end to pivot about pivot 411.

As shown in FIGS. 12 and 13, the static (fixed) jaw 400 can be a curved structure such that a distal section thereof is elevated relative to the proximal section. The static jaw 400 can have an opening formed therein through which the movable jaw 410 passes. The movable jaw 410 is also a curved structure in that a proximal portion lies within a recess formed in the static jaw 400 and a distal portion passes through the window in the jaw 400. The distal end of the jaw 400 lies above the distal end of the jaw 410 and represents a top portion of the needle receiving groove while the distal end of the jaw 410 represents the bottom portion of the groove.

Figure 14:
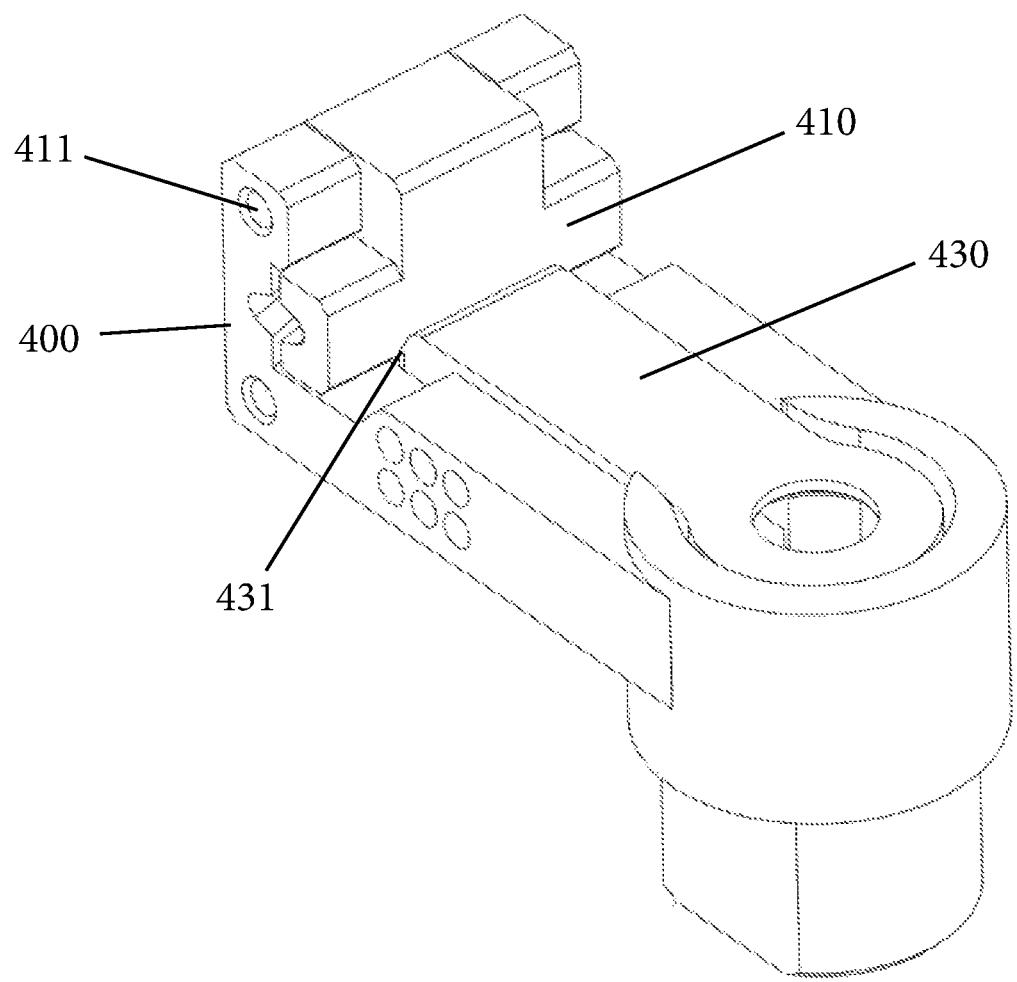
FIG. 14 is a perspective view of an alternate gripper design.
Figure 15:
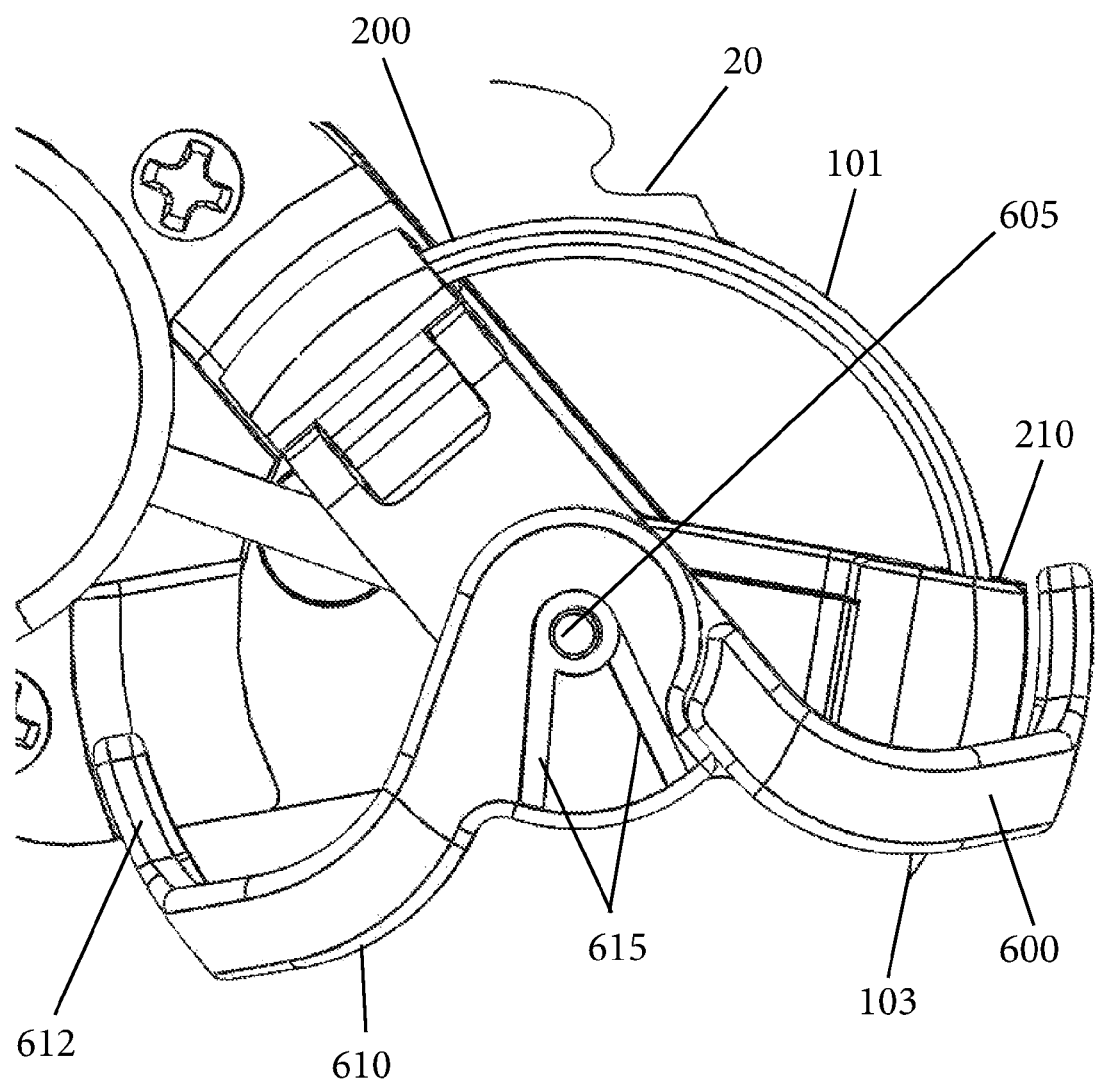
FIGS. 15-18 are various views of one exemplary safety shield mechanism.
Figure 16:
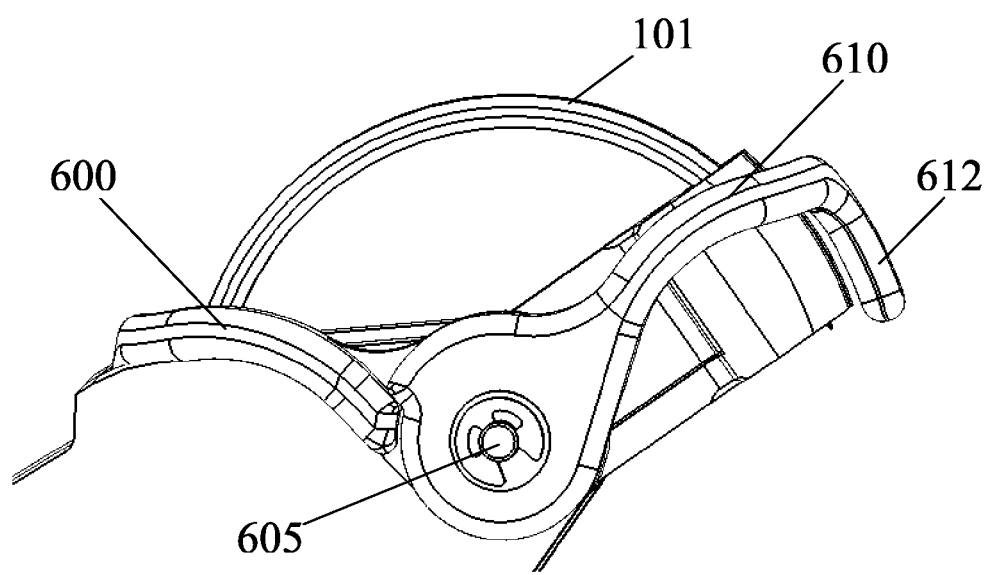
Figure 17:
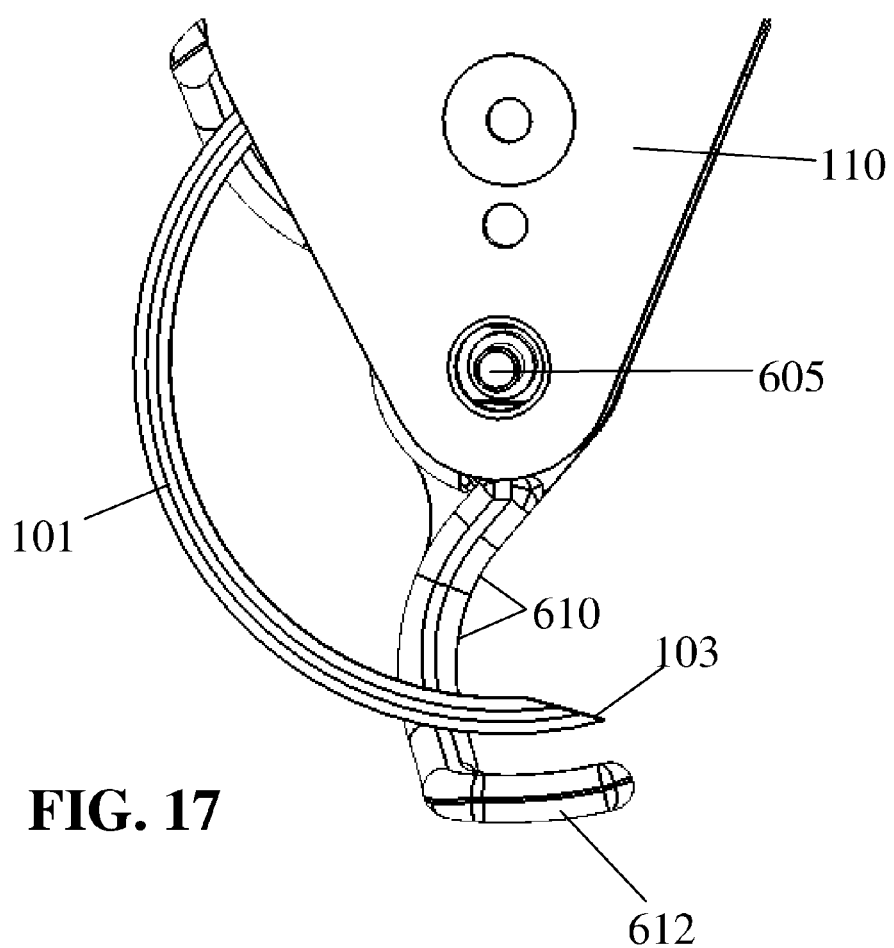

FIG. 14 shows an alternative gripper design. In this design, there is an element 430 that lies within a recess of the fixed jaw 400. The movable jaw 410 is pivotally attached to jaw 400 at pivot 411. In this construction, the element 430 selectively applies a force to the movable gripper 410 to cause a pivoting motion. The element 430 is in the form of a lever or pin that is contacted by the bearing 250 and rotation of the bearing 250 selectively applied a force to the lever 430 (such as pressing down on one end of the lever) resulting in the lever 430 moving a cam surface 431 at a distal end of the lever 430 contacting the moving jaw 410 to cause pivoting thereof. In the illustrated embodiment, the bearing 250 contacts a boss that is part of the element 430 and the rotation of the bearing 250 (as a result of the crankshaft 240 being driven) results in the element 430 being pushed down at one end causing the opposite end to contact and move the movable gripper 410.

This exemplary design has the advantage of a rigid wedging element (lever 430) preventing the separation of the jaws 400, 410 and consequently the release of the needle. Many alternative wedge-based locking/unlocking concepts can easily be recognized, however.

In one embodiment shown in FIG. 13, each gripping mechanism 200, 210 can be a biased mechanism in that the gripping mechanism 200, 210 can be biased to assume one position as a result of the applied biasing force. More specifically, the lever 430 or the movable jaw 410 can be biased (as by being coupled to a biasing element 455, such as a spring or the like as shown in FIG. 13. The bias force applied to the lever 430 or movable jaw 410 causes the movable gripper 410 to assume an open position in its normal state. In FIG. 13, the spring 455 is disposed between the movable gripper 410 and the static (fixed) gripper 400 at the proximal end thereof.

The grippers 400, 410 can thus open and close in a pliers-like fashion that is activated and deactivated by the dual-state eccentric bearing 250. As described herein, the movable gripper 410 pivots about the hinge pin 420 between open (unclamped) and closed (clamped) positions.

As mentioned, the active (grip) condition and the default (release) condition are energized by the rotating crankshaft 240 and bearing 250 when this bearing 250 is at its high point and low point, respectively. In the current embodiment, the gripping force on the needle 101 can be altered by changing the diameter or degree of eccentricity of the bearing 250, which changes the displacement of the movable gripper 410. The gripping force can also be varied by modifying the distance relationship between the length of the lever arm of the movable gripper 410 and the length from the hinge pin 420 to the gripping means needle groove 405. In this embodiment, the lever arm enables the device to amplify the load input into the gripping system at a 3:1 ratio, although it is easy to recognize that higher or lower ratios can be utilized in order to provide a gripping force performance similar to a standard needle driver. Furthermore, the surface of the needle groove 405 can be altered with notches, ribs, detents, roughness, or similar modifications in order to enhance the gripping force on the needle 101 and to prevent the needle from pitching, rolling or pulling-out of the gripping means.

It will be appreciated that the cross-sectional geometry of the groove 405 in the gripping means provides an effective gripping interface between the two at the location at which the two are in intimate contact. For example, the interface can be defined as a V-shaped notch, trapezoidal shape, or other geometry thereby creating a matched or compatible fit between the needle and the gripping means. It will be appreciated that the shapes of the notch and needle can be different, i.e., round, oval, hexagonal, so long as preferably there is the above-described match fit between the two resulting in an effective needle gripping location. Further, the cross-sections of the needle and the receiving groove can be different from each other so as they achieve consistent alignment and sufficient gripping force.

There are two (first and second) safety guards 600, 610 depicted in FIGS. 11 and 15-18 that are located at the distal end of the device 100 and protect the user from the sharp point 103 of the needle 100. In the illustrated embodiment the safety guards 600, 610 pivot on a shared axis 605, which is also the axis of rotation of the needle 101 and the axis about which the handle 110 pivots (rotates). The guards are biased to each other and to the housing 110 by torsion springs 615, although leaf springs, molded-in plastic springs, elastomers, and the like can create suitable biasing means. In the current device, the first safety guard 600 is biased to the housing 110 and shields the needle point when the device 100 is in its at-rest position or when the second gripping means is retracted. Moreover, the second safety guard 610 is biased to the first safety guard 600 and shields the needle 101 from the user when the needle point 103 exits the tissue 10. The biased connections of the two safety guards 600, 610 enable the first safety guard 600 to rotate in concert with the device 100 as the user rotates the device into and through the tissue 10 and the second safety guard 610 to follow the first.

If the user reverses the rotational insertion of the needle, the biasing means (springs 615) returns the safety guards 600, 610 to their original positions. The bias between the safety guards 600, 610 also allows them to flexibly and reversibly extend away from each other and contour themselves to the tissue being sutured. This can be particularly useful when the tissue is not flat. The second safety guard 610 is positioned away from the needle point 103 when the device 100 is at-rest, however, is seated on the tissue, and therefore protecting the user from the needle point when the needle 101 emerges from the tissue 10. In addition to protecting the user from the needle point, the second safety guard 610 also visually identifies the tissue exit location of the needle 101. In the current embodiment, the second safety guard 610 is comprised of a strut 612 that is physically aligned with the needle plane and provides visual location feedback to the user. It will be understood that other location identifiers alignment features such as cross-hairs, rings, slots, markings and the like can be utilized in order to achieve the same end. The strut of each safety guard 600, 607 thus provides an alignment feature to the user since the user understands that the needle 101 will pass just inside the strut. For example, if the needle is being advanced through the tissue and is not visible, the user knows, it will pass just inside the strut of the safety guard resting on the tissue as it exits.

Figure 18:
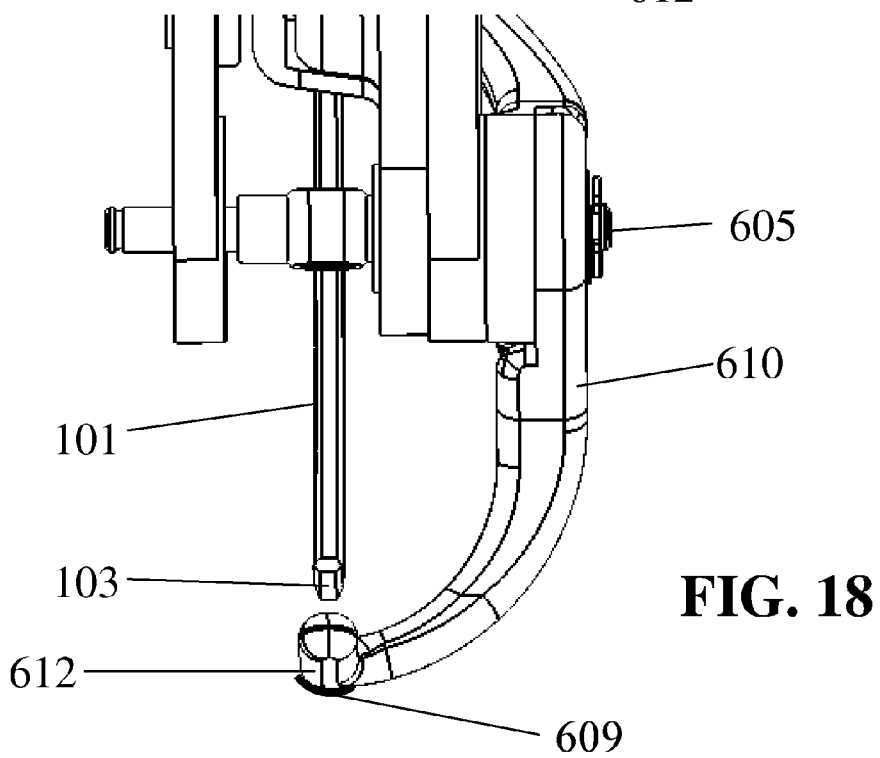
Figure 19:
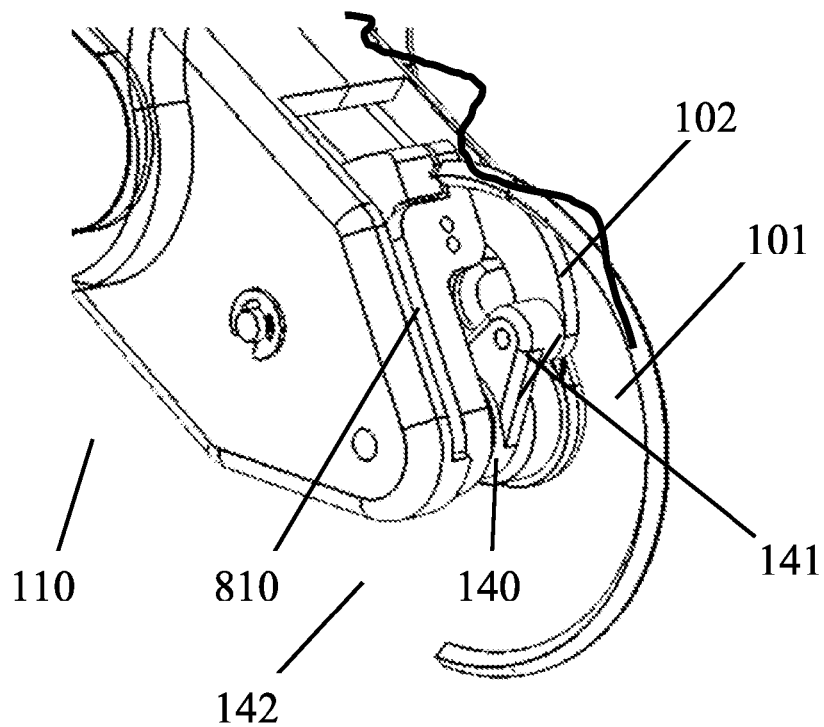
FIGS. 19-26 are various views of an alternative needle gripper construction.
Figure 20:
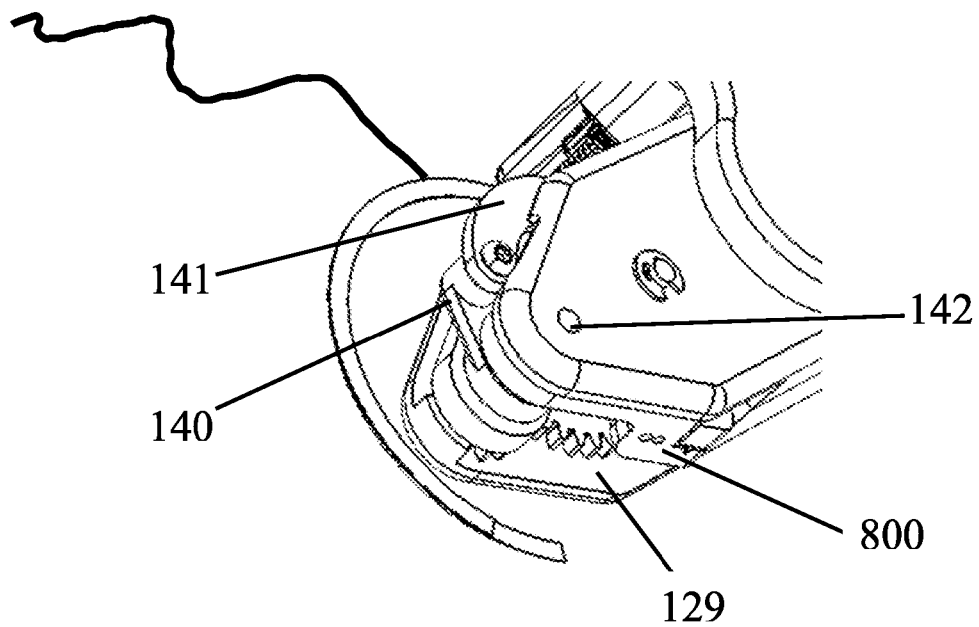
Figure 21:
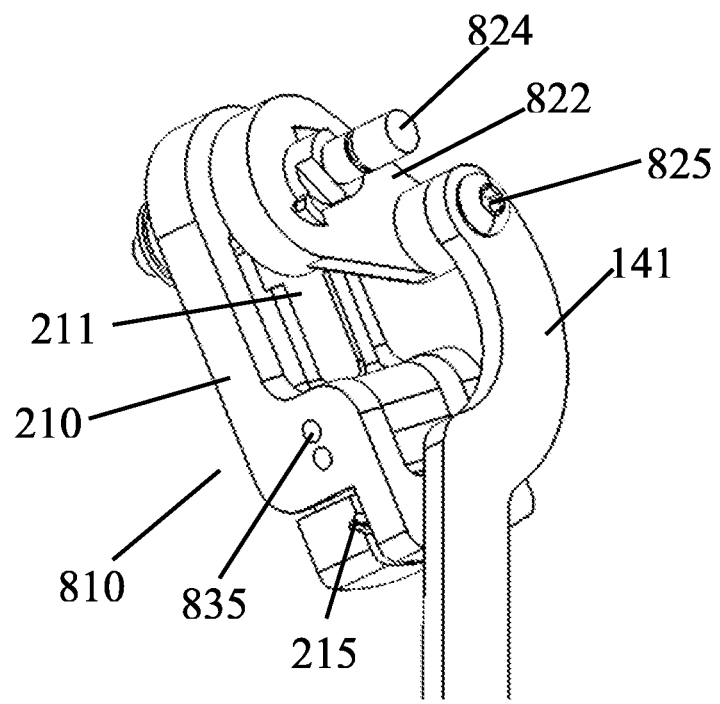
Figure 22:
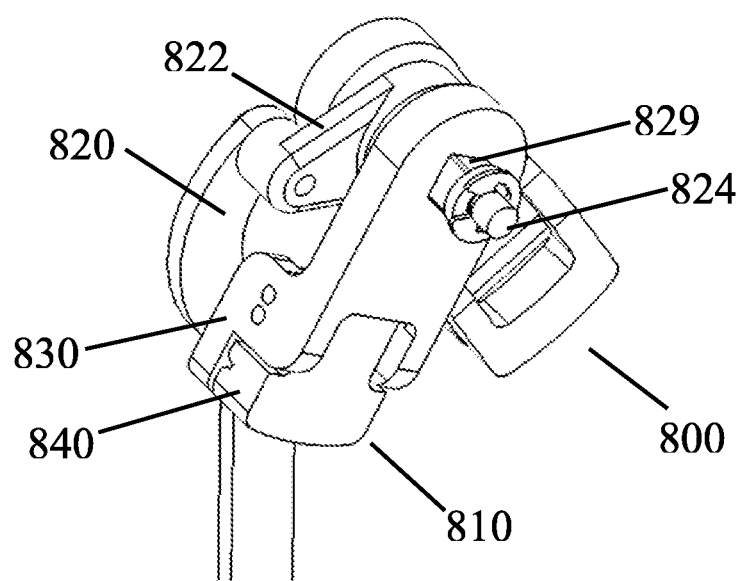
Figure 23:
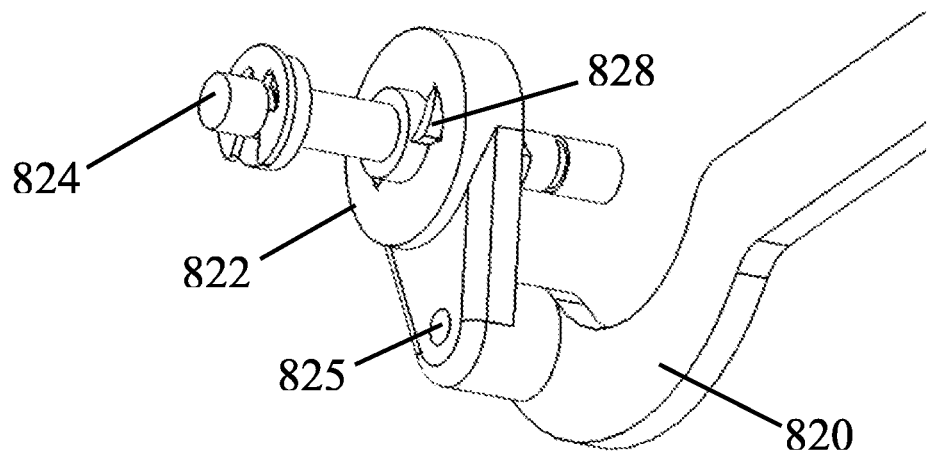
Figure 24:
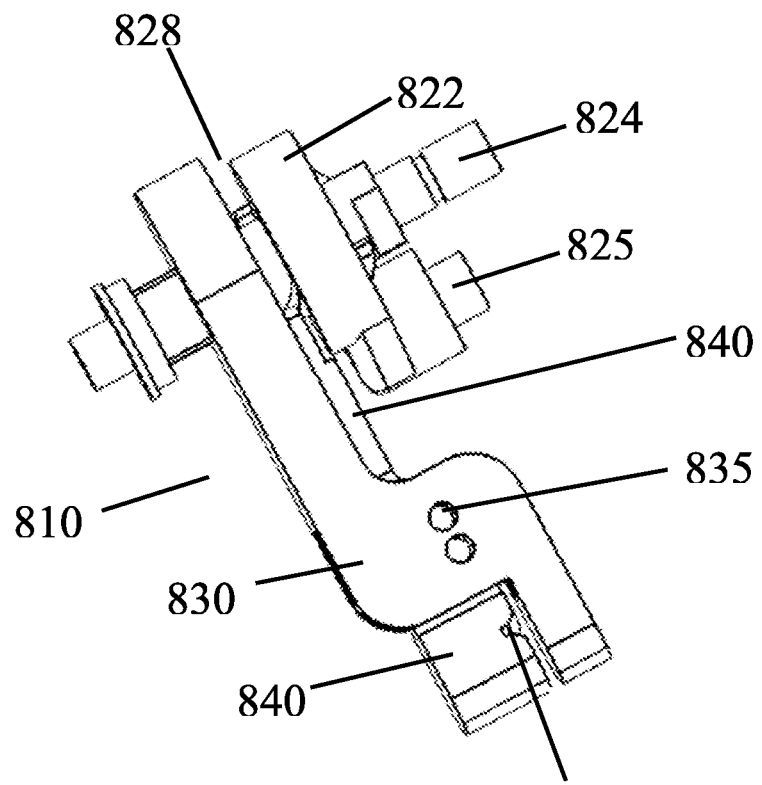
Figure 25:
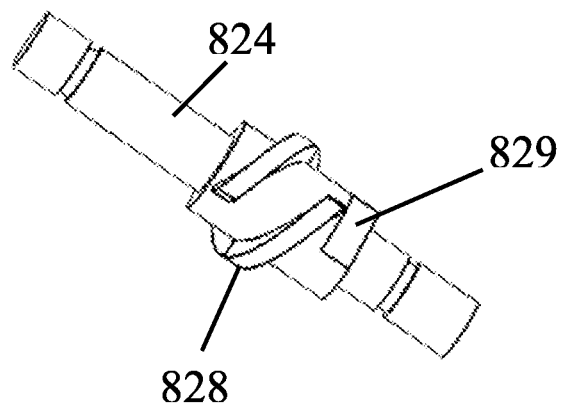
Figure 26:
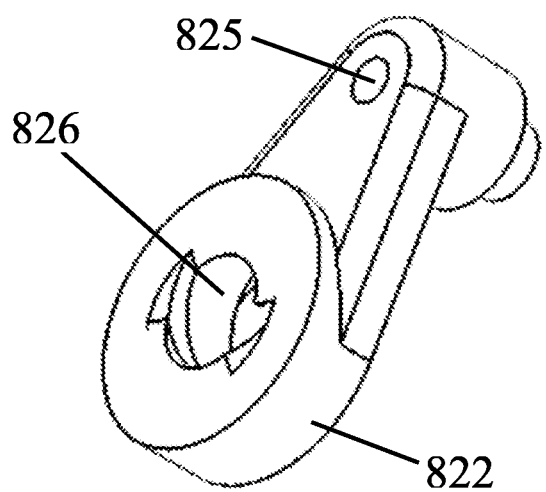

The safety guards 600, 610 are merely exemplary and the guards can take any number of different forms so long as they perform the intended function. For example, the guards can be cage-like as disclosed in commonly owned U.S. patent application Ser. No. 13/584,536, which is hereby incorporated by reference in its entirety, or constructed from a frame-work of formed wire or plastic and can be formed of one or more components and its rotation may be constrained by a spring or other suitable means as shown. Further, the spring element may be integral to the framework, e.g., a wire form constructed of spring tempered steel or nickel titanium alloy which possess substantial elasticity. It features a spring bias that predisposes the shield towards covering the needle point when the device is in its ready to penetrate configuration. As shown in FIG. 18, a tissue contacting surface of each strut of the suture guards 600, 610 can include a modified surface (front and/or bottom surface of strut) 609 that enhances gripping/interference between the guard and the tissue (or other object, like a catheter) so that the guard rotates away from the needle point and positions second guard at the needle exit site. The modified surface 609 can be 3-D structures (barbs, dots, etc.) or can be rough surface or other texture that promotes enhanced gripping with tissue (skin).

Finally, a suture cutter 700 that is integral to the handle would provide the user with a means to cut and trim suture 20 during the procedure. The cutter 700 is an internal dynamic shearing apparatus, i.e., scissors or slideable blade(s) that would require the user to press or slide a button 710 in order to activate a blade 720 to cut the suture 20. The button 710 directly or indirectly translates the blade 720 across the suture 20 and into a slot that is functionally narrow, providing a holding surface for the suture and allowing only the blade to travel therethrough. This means could be a slideable track if the button 710 were to slide in the direction of the blade 720, or a pair of matched ramps that would convert the vertical motion of the depressed button 710 to a horizontal motion of a cutting blade 720. Further the blade 720 may act in a pivoting manner that slices across the suture 20. A spring or other suitable means 730 returns the button 710 to its original position. Further, the suture 20 is positioned in a notch 740 (dog-legged, slot, or hole) on the outer surface of the housing 110 in order for the user to cut it to a predetermined or greater length.

In this preferred embodiment, the position of the cutter blade 720 relative to the surface of the housing 110 determines the length of the cut suture tail. Also, the cutter blade angle directs the suture 20 into the terminus of the dog legged slot 740 in order to optimize the cutting action.

In use of the preferred embodiment device, the user removes the device 100 from its sterile packaging in its at rest position with the needle tip enclosed by the second gripping mechanism 210 and the proximal end of the needle gripped by the first gripping mechanism 200. The user then grips the device 100. In a preferred embodiment, the user grips the device 100 between his/her thumb and one or more fingers with the user's thumb on the actuator 125.

The user then depresses the actuator 125, retracting the second gripping mechanism 210, exposing the needle tip 103, and winding-up the energy storage mechanism.

The user then positions the needle tip 103 against the tissue 10 to be sutured and passes the needle tip 103 through the tissue 10 by rotating the housing 110 in an arcing motion until the needle tip 103 emerges from the tissue 10. The second safety guard 610 surrounds or shields the needle point 103 from the user.

Next, the user slightly and controllably releases his grip on the actuator 125, allowing the return spring 130 to move the actuator 125 into its initial at-rest position, and, in so doing, rotates the second gripping mechanism 210 to re-engage the distal tip 103 of the needle 101. When the actuator 125 reaches the end of its stroke at the at-rest position, the pawl 220 releases the wound-up torsion spring energy in the energy storage mechanism, causing the crankshaft 240 and bearing 250 to rotate one half turn (i.e., 180 degrees), thereby switching the state of the gripping mechanisms 200, 210 such that the first gripping mechanism 200 is now released and the second gripping mechanism 210 grips the distal end 103 of the needle 101.

Next, the user depresses the actuator 125. The second gripping mechanism 210, now gripping the needle 101, rotates from the at-rest position to the retracted position, and in so doing, actively and rotationally extracts the needle 101 from the tissue 10. This actuator movement also winds-up the energy storage mechanism for its next action.

Still depressing the actuator 125, the user lifts the device 100 from the tissue, pulling a length of suture 20 through the tissue 10. The user then releases his/her grip on the actuator 125, allowing it to rotate back to the at-rest position, and in so doing rotating the second gripping mechanism 210 to its at rest position, releasing the stored spring energy in the energy storage mechanism, rotating the crankshaft and bearing, and switching the state of the gripping mechanisms 200, 210 to its original condition where the first gripping mechanism 200 grips the proximal end 103 of the needle 101 and the second gripping mechanism 210 has released the needle 101, yet still covers the needle point 103.

Finally the user ties the suture 20 to form a stitch and trims the suture near the knot, leaving the user holding the device 100 in exactly the same condition as when it was removed from the package, except for a slightly shorter length of suture. The device 100 is now ready to deliver additional sutures.

Now referring to FIGS. 19-26 in which alternative first and second needle grippers 800, 810 are shown. As with the previous embodiments disclosed herein, the first and second needle grippers 800, 810 are operatively coupled to an actuator, such as actuator 125, by means of a linkages (i.e., the first and second linkages described herein) or some other mechanical means (belts, cables or other means known to the art) such that when the actuator moves from its at-rest position to its fully depressed position, the second needle gripper 810 moves proportionally from its at-rest position to its fully retracted position. In the illustrated embodiment, the actuator assembly comprises actuator assembly 125 as described herein including the windup mechanism and crankshaft ratchet assembly, and the pawl 220.

As in the previous embodiment, an energy mechanism serves to reciprocally activate the first and second needle grippers 800, 810 in order to effect the gripping, releasing, and the transferring of the needle 101. When one of the first and second needle grippers 800, 810 is activated to grip the needle 101, the other of the first and second needle grippers 800, 810 is deactivated and releases the needle 101.

In one embodiment, the connection between the needle gripper and actuator is comprised of a connecting arm 820, threaded nut 822 and threaded axle 824. In summary, the motion of the connecting arm 820 creates the alternate gripping-releasing of the first and second needle grippers 800, 810 by rotating and translating the threaded nut 822 along the stationary threaded axle 824 into and away from the respective first and second needle grippers 800, 810.

Specifically, the connecting arm 820 is generally axially oriented relative to the device housing and is connected by a generally rigid mechanical means to the actuator. Further it is pivotably attached to the threaded nut 822 via a nut pivot 825. The threaded nut 822 features an internal thread 826 that intimately surrounds and engages a threaded axle flight 828 of the threaded axle 824. This axle 824 is held stationary i.e., non-rotating, via the engagement between a threaded axle flat 829 and the first needle gripper 800. Note that the flat 829 can be another configuration, e.g., square, hexagonal, pinned, and can be located anywhere along the axle 824 such that it engages the housing 110, static clamp or jaw 830 or other component restricting its rotation. It is this stationary condition of the threaded axle 824 that allows the threaded nut 822 to rotate about the axle's axis and translate toward and away against the moving clamp or jaw 840 of one of the first and second needle grippers 800, 810. When the threaded nut 822 compresses that respective moving jaw 840 of the moving second needle gripper 810, which is comprised of the moving jaw 840 and static jaw 830, the second needle gripper 810 is activated to firmly grip the needle 101.

Another result of the threaded nut 822 engaging the moving jaw 840 of the second needle gripper 810 is that the nut 822 has separated completely from the moving jaw 840 of the non-rotating first needle gripper 800, and in a direct effect has deactivated the gripping condition of that first needle gripper 800. This opening action of the moving jaw 840 may be aided by a spring or other biasing means that facilitates the release of the needle 101 by the first and second needle grippers 800, 810. This may be advantageous for releasing the needle but also in biasing the first and second needle grippers 800, 810 such that it is configured in its open condition to readily accept the needle in the subsequent transferring phase.

Figure 27:
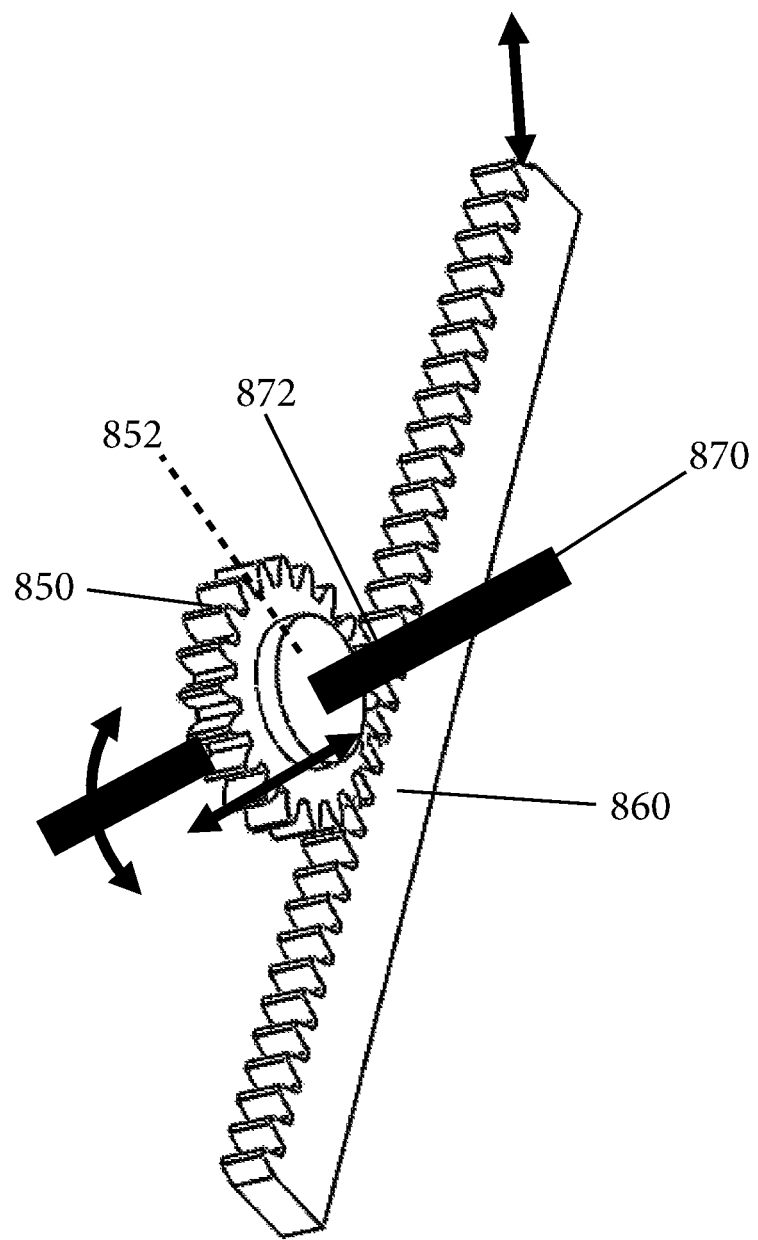
FIGS. 27-28 are various views of another alternative needle gripper construction.

FIG. 27 presents alternative means for activating a threaded nut 850 comprising an internal thread 852, and oscillating the nut 850 into and away from the first and second needle grippers 800, 810. FIG. 27 illustrates that threaded nut 850 is simultaneously rotated and traversed by the axial displacement of a rack 860, which is coupled to the actuator 125. As the actuator is depressed, the rack 860 moves tangentially across the nut 850 and rotates the nut whose threads 852 are engaged intimately with the threads 872 of the stationary threaded axle 870. At the same time the nut 850 is rotating, it is traversing laterally along the axle threads 872 and towards the first and second needle grippers 800, 810 due to the pitch of the threads. This action creates the travel and force required to activate and deactivate the respective first and second needle grippers 800, 810 through alternately compressing the respective moving jaws 840 of the first and second needle grippers 800, 810.

Figure 28:
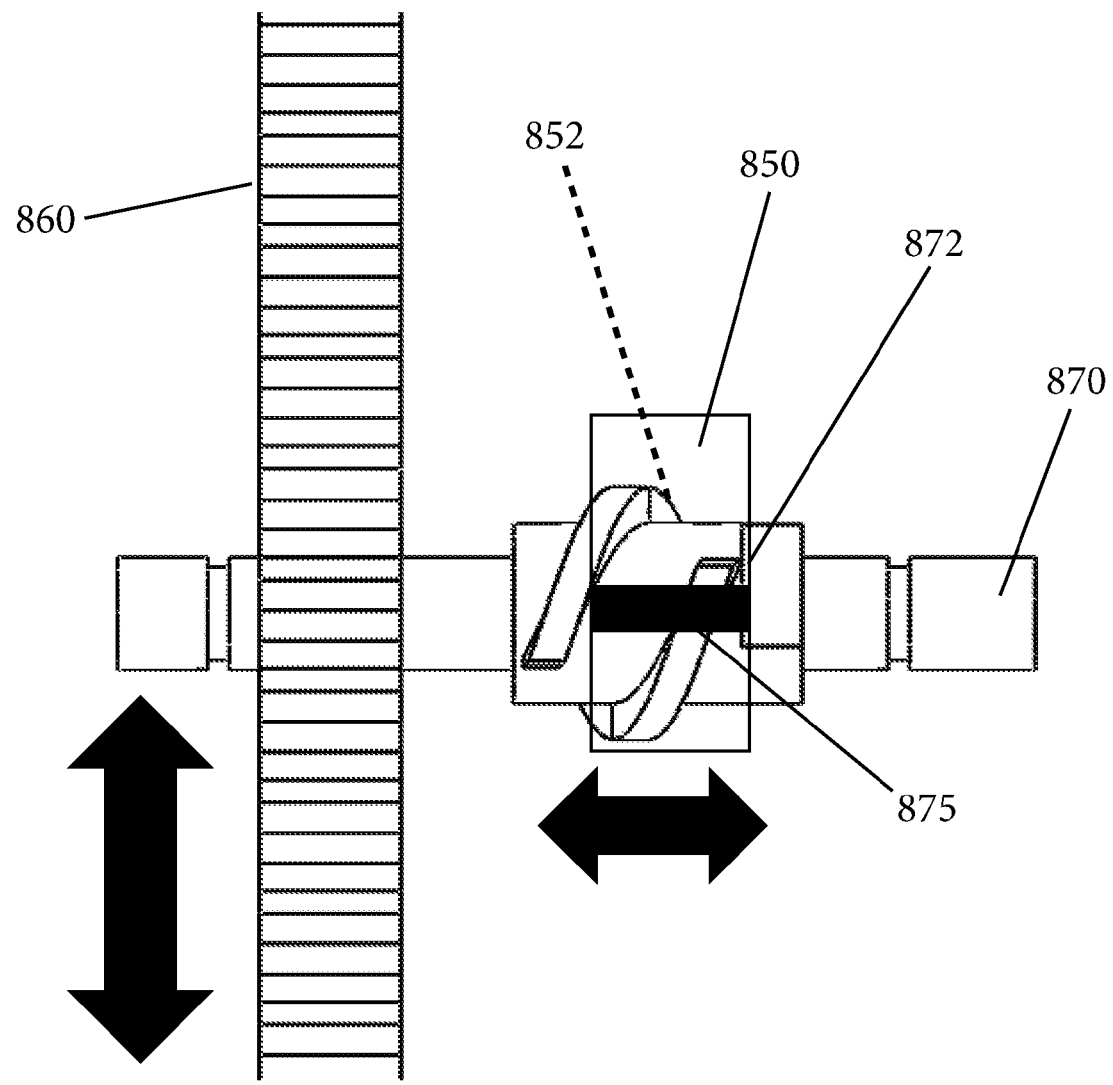

FIG. 28 illustrates another mechanism for activating the first and second needle grippers 800, 810 via the threaded nut 850. As in FIG. 27, the nut 850 traverses across the threaded axle 870, however, the rack 860 in this mechanism acts upon and rotates the threaded axle 870, and not the nut 850. This rotation causes the nut 850 to traverse, but not rotate, such that it activates and deactivates the first and second needle grippers 800, 810. Rotation of the nut 850 is inhibited by a single or multiple tabs 875 projecting from the nut and engaging a single or pair of corresponding grooves in the housing 110 or similar stationary feature. These tabs 875 however are able to slide laterally, freely and guide the nut 850 during its traverse.

Figure 29:
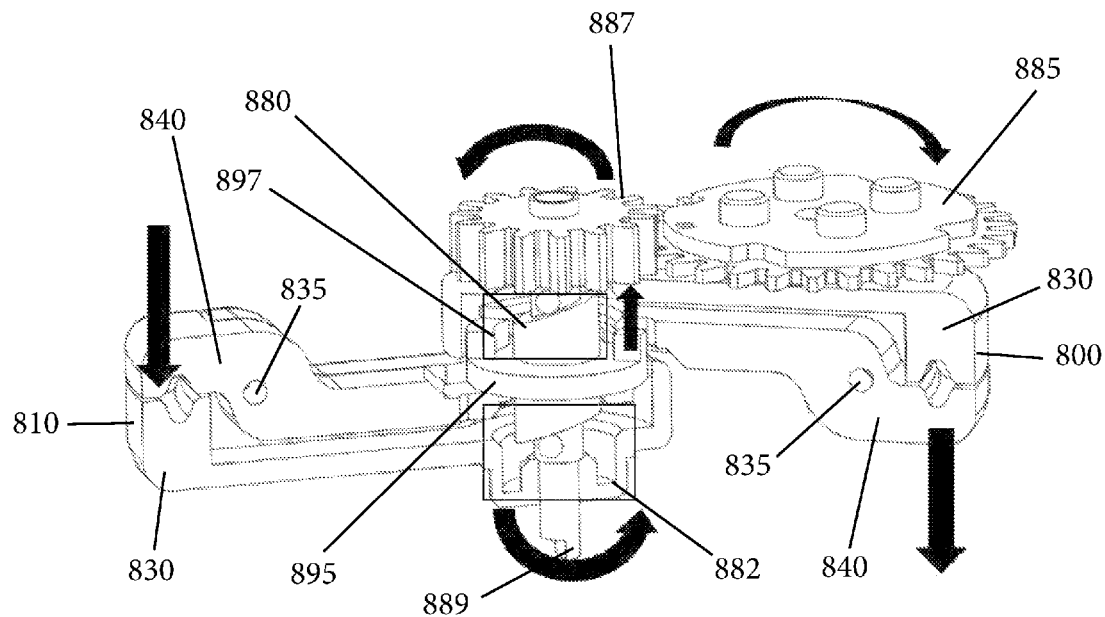
FIGS. 29-30 are various views of yet another alternative needle gripper construction.
Figure 30:
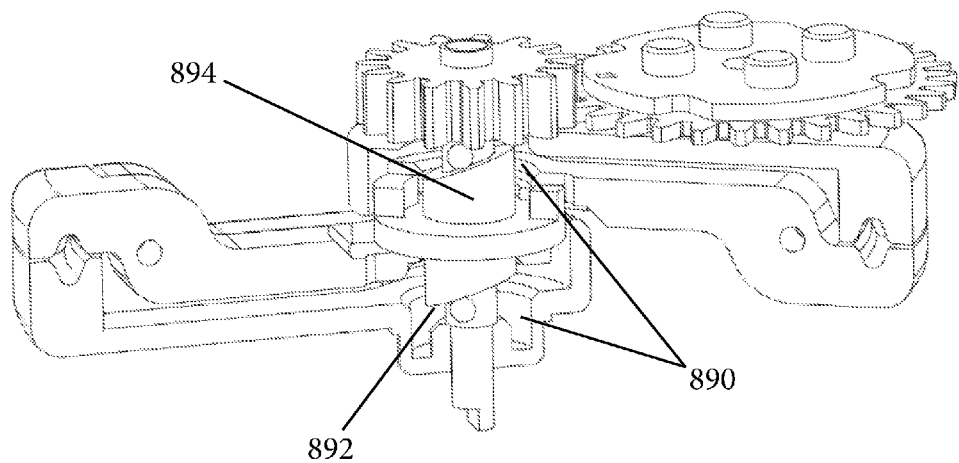

Yet another variation for first and second needle grippers 800, 810 activation by way of a traversing nut is depicted in FIGS. 29 and 30. As mentioned, the first and second needle grippers 800, 810 are comprised of static jaw 830, moving jaw 840 and hinge pin 835. In this embodiment, two springs 880, 882 apply alternating forces to the respective moving jaw 840 in order to grip and release needle 101. More specifically, drive gear 885 is rotated by the movement of actuator 125 and rotates axle gear 887, which is rigidly coupled to rotating axle 889. Further, this rotating axle 889 features one or more axle pins 890 that engage and follow the nut's cam surfaces 892, 894 and as a result, translate the nut 895 toward and away from the first and second needle grippers 800, 810. The nut tab(s) 897 engage a rotation stop in static jaw 830 of the non-rotating first needle gripper 800 so that the nut 895 does not rotate, but rather translates. FIG. 29 shows a condition in which the nut 895 has translated towards the non-rotating first needle gripper 800 and has compressed spring 880 such that spring 880 cannot apply a force to moving jaw 840, but has allowed spring 882 to elongate and apply its full force to the moving jaw 840 of the moving second needle gripper 810. In this condition, the first needle gripper 800 has released the needle 101 and second needle gripper 810 has gripped it. It is through this mechanism that the needle 101 is gripped and released by the first and second needle grippers 800, 810.

Although the actuator 125 has been mentioned as the direct input force provider into these systems, please understand that there are multiple mechanisms that may couple the actuator and the nut-driven gripping assemblies. For example, a rotational windup system comprising a torsion or other spring type can store energy and release it in order to rotate the nut or axle. Further, a linear system comprising a rod, linkage or the like can be utilized to rotate the nut or axle. And, a hybrid of rotational and linear mechanisms may also be used to perform these functions. The above examples may further comprise a clutch or ratcheting system that holds the stored energy until such time that the user wishes to cycle the mechanism or a trip feature such as a pawl, lynch pin, or similar automatically cycles the mechanism. These systems may also rely on a unidirectional rotation of a crankshaft or axle, or a rotation that may oscillate clockwise-counter-clockwise. Therefore it is easily understood that multiple mechanisms can serve to activate a nut-driven needle gripping device.

Figure 31:
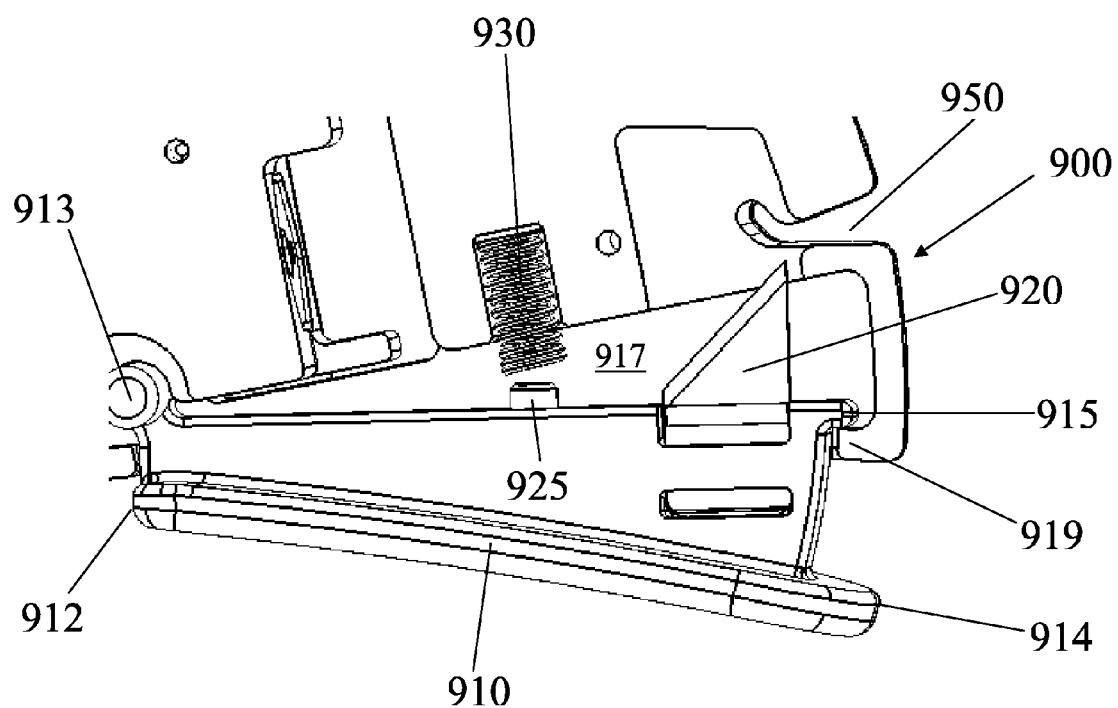
FIG. 31 is a cross-sectional view of an alternative suture cutter.

FIG. 31 shows an alternative cutter arrangement. In this embodiment, the cutter mechanism 900 is of a pivotable, non-linear actuated type. The cutter mechanism 900 includes a cutter body 910 that has a first end 912 that is pivotally attached to the housing 110 (at pivot 913) and an opposite second end 914 that is a free end. The cutter body 910 holds a blade 920 that faces inward toward the housing 110. The cutter body 910 includes a lip 915. The housing 110 includes a space 917 for receiving the cutter body 910 in the fully retracted cutting position thereof. The space 917 terminates at the proximal end of the housing 110 and includes a catch (lip) 919. The lip 915 is received within the space 917 and when the lip 915 contacts the catch 919, the outward movement of the cutter body 910 is limited since the engagement of lip 915 to catch 919 serves as a stop. A biasing member, such as a spring 930, is disposed within the housing 110 and is disposed partially within the space 917. The spring 930 is shown in a fully extended (rest) position in the figure. An inner surface of the cutter body 910 includes a protrusion 925 facing the housing 110. The protrusion contacts the spring 930 when the cutter body 910 is pushed into the space 917 for cutting the suture. The blade 930 is received within a blade receiving space 917 of the housing 110 and a notch 950 is in communication with the blade receiving space 917.

Based on the foregoing, it will be appreciated that the device 100 provides a single actuator that can be used with one hand and allows the user to complete one actuator cycle by pressing and then releasing the single actuator two times. All of this can be done with a single hand during the procedure. In addition, the present device can be provided such that the actuator and cutter can be located on the same side of the device to allow the user to use the same thumb to operate both.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing, the actuator being operatively coupled to: (a) a first linkage that pivots the second needle gripper between a fully extended position and a retracted position relative to the housing; and (b) a second linkage that is operatively coupled to the first and second needle grippers and configured to alter a state of each of the first and second needle grippers to permit each respective needle gripper to either: (a) receive and grasp the suturing needle or (b) release the suturing needle;
wherein the second linkage includes a one-way clutch that is operatively coupled to the actuator and is configured to synchronously alter the states of the first and second needle grippers to permit each respective needle gripper to either: (a) receive and grasp the suturing needle or (b) release the suturing needle, and wherein the one-way clutch is configured to trip at a select operating state of the actuator to cause a release of stored energy in the second linkage which causes the synchronized alteration of the states of the first and second needle grippers.

2. The device of claim 1, wherein the actuator moves in a sweeping, non-linear motion relative to the housing.

3. The device of claim 1, wherein the first linkage comprises a plurality of gears that operatively couple the actuator to the second needle gripper such that motion of the actuator is translated into the second needle gripper rotating about a first pivot point between the fully extended position and a retracted position.

4. The device of claim 3, wherein the plurality of gears of the first linkage includes a first gear that is associated with the actuator; a second gear that meshes with the first gear; and a third gear that is fixedly coupled to the second needle gripper such that a pivoting movement of the actuator causes the first, second and third gears to rotate resulting in rotation of the second needle gripper.

5. The device of claim 4, wherein the first gear is a fan gear and the second gear is a reducer gear that is configured such that the second needle gripper rotates a greater number of degrees than the actuator.

6. The device of claim 1, wherein the second linkage comprises an energy storage mechanism that is configured to store energy during an inward stroke of the actuator and release the stored energy during one stage of an outstroke of the actuator, whereby the release of the stored energy causes the states of the first and second needle grippers to be altered.

7. The device of claim 6, wherein the one stage of the outstroke comprises a final stage of the outstroke.

8. The device of claim 1, wherein each of the first and second needle grippers comprises a first clamp and a second movable clamp that is pivotally attached to the first clamp at a pivot to permit the second movable clamp to pivot between open and closed positions, each of the first clamp and the second movable clamp defining a needle receiving groove in which the suturing needle is captured.

9. The device of claim 8, wherein the second movable clamp is biased to the open position.

10. The device of claim 8, wherein the second linkage includes a part that applies a force to the second movable clamps of the first and second needle grippers in an alternating manner to cause the reciprocal opening and closing of the first and second needle grippers.

11. The device of claim 1, further including a safety shield mechanism for shielding the suturing needle, the safety shield consisting of first and second guards that pivot on a shared axis, the first and second guards being biased to each other and to the housing by a plurality of biasing elements.

12. The device of claim 1, wherein the one-way clutch automatically trips at the select operating state of the actuator by contacting a structure associated with the housing.

13. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing, the actuator being operatively coupled to: (a) a first linkage that pivots the second needle gripper between a fully extended position and a retracted position relative to the housing; and (b) a second linkage that is operatively coupled to the first and second needle grippers and configured to alter a state of each of the first and second needle grippers to permit each respective needle gripper to either: (a) receive and grasp the suturing needle or (b) release the suturing needle;

wherein the second linkage includes a one-way clutch that is operatively coupled to the actuator and is configured to synchronously alter the states of the first and second needle grippers to permit each respective needle gripper to either: (a) receive and grasp the suturing needle or (b) release the suturing needle;

wherein the second linkage comprises an energy storage mechanism that is configured to store energy during an inward stroke of the actuator and release the stored energy during one stage of an outstroke of the actuator, whereby the release of the stored energy causes the states of the first and second needle grippers to be altered;

wherein the energy storage mechanism includes a windup mechanism and a crankshaft assembly whose operation alters the states of the first and second needle grippers, the windup mechanism includes a first spring that stores energy during the inward stroke of the actuator as a result of a coupling between the actuator and the windup mechanism and release the stored energy during the one stage of the outstroke of the actuator, the windup mechanism being configured to selectively engage and interlock with the crankshaft assembly, the crankshaft assembly being maintained in a held position until the one stage of the outstroke at which time the crankshaft assembly is released from the held position and the windup mechanism releases its stored energy resulting in the crankshaft assembly rotating a predetermined number of degrees.

14. The device of claim 13, wherein the windup mechanism rotates 180 degrees in a first direction during the inward stroke of the actuator and during the one stage of the outstroke, the windup mechanism and the crankshaft assembly rotate 180 degrees in an opposite second direction.

15. The device of claim 13, wherein the one-way clutching comprises a portion of the windup mechanism, a portion of the crankshaft assembly and a pawl that selectively engages the crankshaft assembly to restrict movement of the windup mechanism and the crankshaft assembly until the one stage of the outstroke.

16. The device of claim 13, wherein the windup mechanism includes a torsion spring that is fixed to the housing at a first end and has a second end that is fixed to a pinion gear that is coupled to the actuator by a rack that moves when the actuator moves relative to the housing such that movement of the actuator is translated into rotation of the pinion gear and rotation of the windup mechanism, the windup mechanism further including a windup ratchet that is fixedly attached to the pinion gear and rotates therewith.

17. The device of claim 16, wherein the windup ratchet has a pair of windows formed therein that selectively receive a pair of first flexible tabs that are part of a crankshaft ratchet that is part of the crankshaft assembly to releasably interlock the windup ratchet to the crankshaft ratchet, the pair of windows being formed 180 degrees apart from one another and the pair of first flexible tabs being formed 180 degrees apart from one another, the crankshaft ratchet being fixedly connected to a crankshaft that drives the movements of the first and second needle grippers.

18. The device of claim 17, wherein the crankshaft ratchet includes an anti-reverse feature to prevent rotation of the crankshaft during the inward stroke of the actuator.

19. The device of claim 18, wherein the anti-reverse feature comprises a pair of second flexible tabs formed as part of the crankshaft ratchet, wherein the second flexible tabs contact a portion of the housing to prevent rotation of the crankshaft ratchet in one direction when the windup mechanism is being wound during the inward stroke.

20. The device of claim 17, wherein the crankshaft assembly includes a stop mechanism to restrict rotation of the crankshaft to a predetermined number of degrees when the windup mechanism releases its stored energy.

21. The device of claim 20, wherein the stop mechanism comprises a body attached to the crankshaft and at least one biased pin slidably disposed within an opening formed in the body such that rotation of the body during the release of energy by the windup mechanism causes the pin to protrude beyond a peripheral edge of the body due to centrifugal force exacted onto the pin and make contact with a fixed stop that is part of the housing resulting in the crankshaft only traveling the predetermined number of degrees when the windup mechanism releases its stored energy.

22. The device of claim 13, wherein the crankshaft includes an eccentrically mounted bearing that is rotated and applies an alternating force to the first and second needle grippers to change the states of first and second needle grippers in a reciprocal manner.

23. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing, the actuator moving from an initial rest position in an inward stroke to a fully retracted position and returns to the initial rest position during an outstroke;
a windup mechanism coupled to the actuator and configured to rotate 180 degrees in a first direction, store energy, and become releasably coupled to a crankshaft assembly during the inward stroke of the actuator, wherein the crankshaft assembly remains stationary during the inward stroke of the actuator, the crankshaft assembly being coupled to the first and second needle grippers; and
a locking mechanism for selectively holding the coupled windup mechanism and crankshaft assembly such that the energy of the windup mechanism remains stored;
wherein during the outstroke of the actuator, the actuator returns to the initial rest position and when the actuator reaches a select point in the return to the initial rest position, the locking mechanism is released causing both the windup mechanism and the crankshaft assembly to rotate 180 degrees in an opposite second direction resulting in each of the first and second needle grippers moving between open and closed positions;
wherein the actuator is coupled to the second needle gripper such that during each of the inward stroke and the outstroke, the second needle gripper moves from one of a fully extended position and fully retracted position to the other of the fully extended position and fully retracted position.

24. A device for suturing tissue comprising:
a housing that has a distal end and a proximal end;
an actuator that is coupled to the housing and moves between two positions when squeezed by a user using the user's thumb or finger, thereby defining the two positions which consist of a first at-rest position where the actuator is not squeezed, and a second fully squeezed position where the actuator has traveled to a mechanically limited end of movement of the actuator;
a curved needle with a distal end having a sharp tissue penetrating point;
a fixed needle gripper disposed within the housing aligned to receive and selectively grip or release a proximal end of the curved needle through an opening in the housing;
a movable needle gripper that swings in an arcing motion concentric with the curved needle and is configured to receive and selectively grip or release the curved needle, and also enclosing and protecting the sharpened tip of the curved needle, the swinging arcing motion terminating in two positions that consist of an at-rest position where the movable needle gripper is in an extended position and is spaced from the housing and encloses the needle tip when the curved needle is gripped at the proximal end by the fixed needle gripper, and a retracted position in which the movable needle gripper swings in the arcing motion into the housing, further, the movable needle gripper is connected to the actuator by a mechanical linkage such that when the actuator is not squeezed, the movable needle gripper is in the at-rest, extended position, and when the actuator is fully squeezed, the movable needle gripper is in its retracted position; and
a clamp activating mechanism employed such that the mechanism selectively causes the fixed needle gripper and the movable needle gripper to exist in either of two states, namely, a first state in which the fixed needle gripper grips the proximal end of said curved needle and the movable needle gripper releases the distal end of the curved needle while in its at-rest position, and a second state where the fixed needle gripper releases the proximal needle end and the movable needle gripper grips the distal needle end, further, while gripping the distal needle end, the movable needle gripper maintaining the grip on the curved needle through the movable needle gripper's entire arcing motion from said at-rest position to said retracted position, further still, the second needle gripper being mechanically connected to the actuator such that the clamp activating mechanism switches from the first state to the second state when the actuator moves from said fully squeezed position to said un-squeezed at-rest position.

25. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing, the actuator being operatively coupled to: (a) a first linkage that pivots the second needle gripper between a fully extended position and a retracted position relative to the housing; and (b) a second linkage that is operatively coupled to the first and second needle grippers and configured to alter a state of each of the first and second needle grippers to permit each respective needle gripper to either: (a) receive and grasp the suturing needle or (b) release the suturing needle;
wherein the second linkage includes a rotatable crankshaft that extends in a longitudinal direction within the housing and rotates within the housing, the second linkage being configured such that that the rotatable crankshaft controllably rotates in defined increments to synchronously alter the states of the first and second needle grippers to permit each respective needle gripper to either: (a) receive and grasp the suturing needle or (b) release the suturing needle.

26. The device of claim 25, further including a rotatable concentric bearing that is affixed to a distal eccentric portion of the crankshaft and engages the first and second needle grippers in a manner that creates two synchronous states for each of first and second needle gripper, the two synchronous states comprising a needle gripping state and a needle release state.

27. The device of claim 25, further comprising: a crankshaft ratchet that is fixedly attached to the crankshaft and along with the crankshaft define a crankshaft assembly; and a windup mechanism that rotationally engages the crankshaft ratchet such that when the windup mechanism is lockingly coupled to the crankshaft ratchet, rotation of the windup mechanism is translated into rotation of the crankshaft ratchet and the crankshaft.

28. The device of claim 27, wherein the energy is stored by the windup mechanism during an inward stroke of the actuator as a result of a coupling between the actuator and the windup mechanism and the stored energy is released during one stage of the outstroke of the actuator.

29. The device of claim 28, wherein the windup mechanism is configured to selectively interlock with the crankshaft ratchet, the crankshaft assembly being maintained in a held position until the one stage of the outstroke at which time the crankshaft assembly is released from the held position and the windup mechanism releases its stored energy resulting in the crankshaft assembly rotating a predetermined number of degrees.

30. The device of claim 28, wherein the one stage of the outstroke of the actuator comprises an end portion of the outstroke.

31. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing, the actuator being operatively coupled to: (a) a first linkage that pivots the second needle gripper between a fully extended position and a retracted position relative to the housing; and (b) a second linkage that is operatively coupled to the first and second needle grippers and configured to alter a state of each of the first and second needle grippers to permit each respective needle gripper to either: (a) receive and grasp the suturing needle or (b) release the suturing needle;

wherein the second linkage includes a one-way clutch that is operatively coupled to the actuator and is configured to synchronously alter the states of the first and second needle grippers to permit each respective needle gripper to either: (a) receive and grasp the suturing needle or (b) release the suturing needle, the one-way clutch having an engaged state in which first and second parts of the second linkage are coupled to one another and a disengaged state in which the first and second parts are free to move relative to one another to cause the states of the first and second needle grippers to be synchronously altered, wherein during an at rest position of the device and an end phase of an instroke of the actuator, the first and second parts are engaged to one another, while during a remaining time of the instroke, the first and second parts are disengaged and rotate relative to one another and during an outstroke of the actuator, the first and second parts are engaged to one another.

32. The device of claim 31, wherein the first part is free to rotate in both a first direction and an opposite second direction, while the second part rotates only in one direction.

33. The device of claim 31, wherein during an instroke of the actuator, the first and second parts are free of attachment to one another until the end phase of the instroke at which time the first and second parts become engaged and wherein during the outstroke of the actuator, the first and second parts remain coupled to one another until the one-way clutch is tripped at an end phase of the outstroke at which time, the first and second parts remain engaged and rotate in unison together to cause the synchronized alteration of the states of the first and second needle grippers.

34. The device of claim 31, wherein the second linkage comprises an energy storage mechanism that is configured to store energy during the instroke of the actuator and release the stored energy during one stage of the outstroke of the actuator, whereby the release of the stored energy causes the states of the first and second needle grippers to be altered.

35. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing, the actuator being operatively coupled to: (a) a first linkage that pivots the second needle gripper between a fully extended position and a retracted position relative to the housing; and (b) a second linkage that is operatively coupled to the first and second needle grippers and configured to alter a state of each of the first and second needle grippers to permit each respective needle gripper to either: (a) receive and grasp the suturing needle or (b) release the suturing needle;
wherein the second linkage includes a one-way clutch that is operatively coupled to the actuator and is configured to synchronously alter the states of the first and second needle grippers to permit each respective needle gripper to either: (a) receive and grasp the suturing needle or (b) release the suturing needle, the one-way clutch having an engaged state in which first and second parts of the second linkage are coupled to one another and a disengaged state in which the first and second parts are free to move relative to one another to cause the states of the first and second needle grippers to be synchronously altered, wherein during an instroke of the actuator, the one-way clutch assumes a disengaged state in which the first and second parts move relative to one another for storing energy and during an outstroke of the actuator, the one-way clutch is in an engaged state in which the first and second parts rotate in unison to allow for release of the stored energy and cause the states of the first and second needle grippers to be synchronously altered.

* * * * *